(12) United States Patent
Hirota et al.

(10) Patent No.: US 7,560,577 B2
(45) Date of Patent: Jul. 14, 2009

(54) CATALYST FOR PRODUCTION OF ETHYLENE OXIDE AND METHOD FOR PRODUCTION OF ETHYLENE OXIDE

(75) Inventors: Hiroyuki Hirota, Yokohama (JP); Hiromi Yunoki, Himeji (JP); Masatsugu Mikawa, Yokohama (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/905,039

(22) Filed: Sep. 27, 2007

(65) Prior Publication Data
US 2008/0091038 A1    Apr. 17, 2008

(30) Foreign Application Priority Data
Sep. 29, 2006   (JP) .............................. 2006-268957

(51) Int. Cl.
*C07D 301/10*   (2006.01)
(52) U.S. Cl. ...................... 549/534; 502/117; 502/263; 502/348; 502/355; 549/536; 549/537
(58) Field of Classification Search ................. 549/534, 549/536, 537; 502/415, 355, 347, 117, 263, 502/348
See application file for complete search history.

(56) References Cited

U.S. PATENT DOCUMENTS

| 4,761,394 A | 8/1988 | Lauritzen |
| 4,908,343 A | 3/1990 | Bhasin |
| 5,057,481 A | 10/1991 | Bhasin |
| 5,063,195 A | 11/1991 | Jin et al. |
| 5,187,140 A | 2/1993 | Thorsteinson et al. |
| 6,600,056 B1 | 7/2003 | Mikawa et al. |

FOREIGN PATENT DOCUMENTS

| EP | 0 266 015 A1 | 5/1988 |
| EP | 0 480 538 A1 | 4/1992 |
| EP | 0 501 317 | 9/1992 |
| JP | 47-020079 | 9/1972 |
| JP | 02-056246 A | 2/1990 |
| JP | 04-317741 | 11/1992 |
| JP | 2000-044331 A | 2/2000 |
| JP | 2002-44331 A | 2/2000 |
| WO | WO 03/070662 | 8/2003 |
| WO | WO 03/072244 A1 | 9/2003 |
| WO | WO 03/072246 A2 | 9/2003 |
| WO | WO 2004/002954 A2 | 1/2004 |

OTHER PUBLICATIONS

European Search Report Application/Patent No. 07117566.5—2104 dated Apr. 11, 2008.

*Primary Examiner*—Bernard Dentz
*Assistant Examiner*—David E Gallis
(74) *Attorney, Agent, or Firm*—Buchanan Ingersoll & Rooney PC

(57) ABSTRACT

A catalyst that enables to produce ethylene oxide in a high selectivity and a method for the production of ethylene oxide using the catalyst are provided. In the catalyst for the production of ethylene oxide, wherein the catalyst component is supported by a carrier, a carrier containing α-alumina as the main component which has at least two peaks in the range of pore diameter of 0.01-100 μm and at least one peak of the above peaks is present in the range of pore diameter of 0.01-1.0 μm in the pore distribution measured by mercury porosimetry is adopted as said carrier.

16 Claims, 20 Drawing Sheets

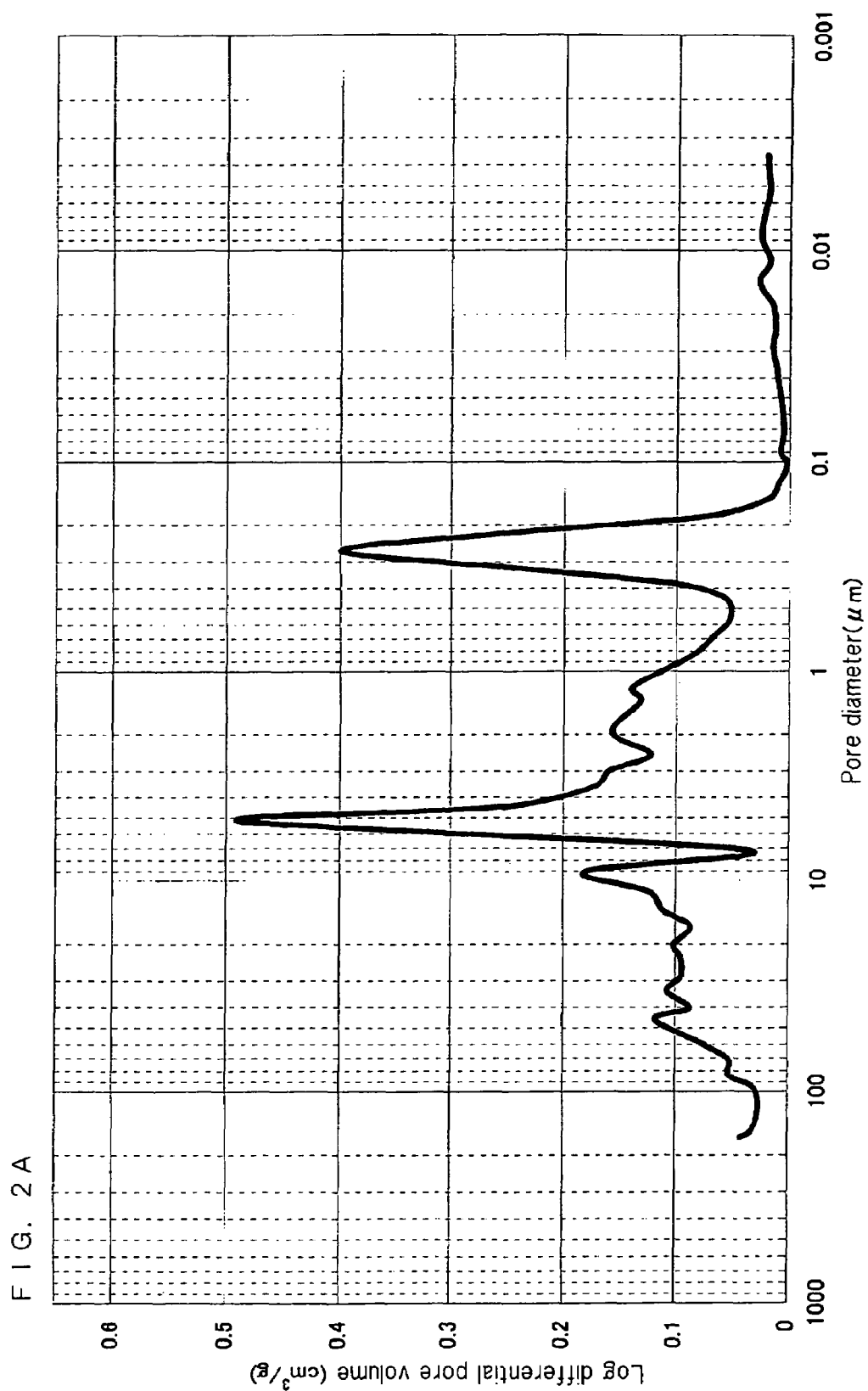

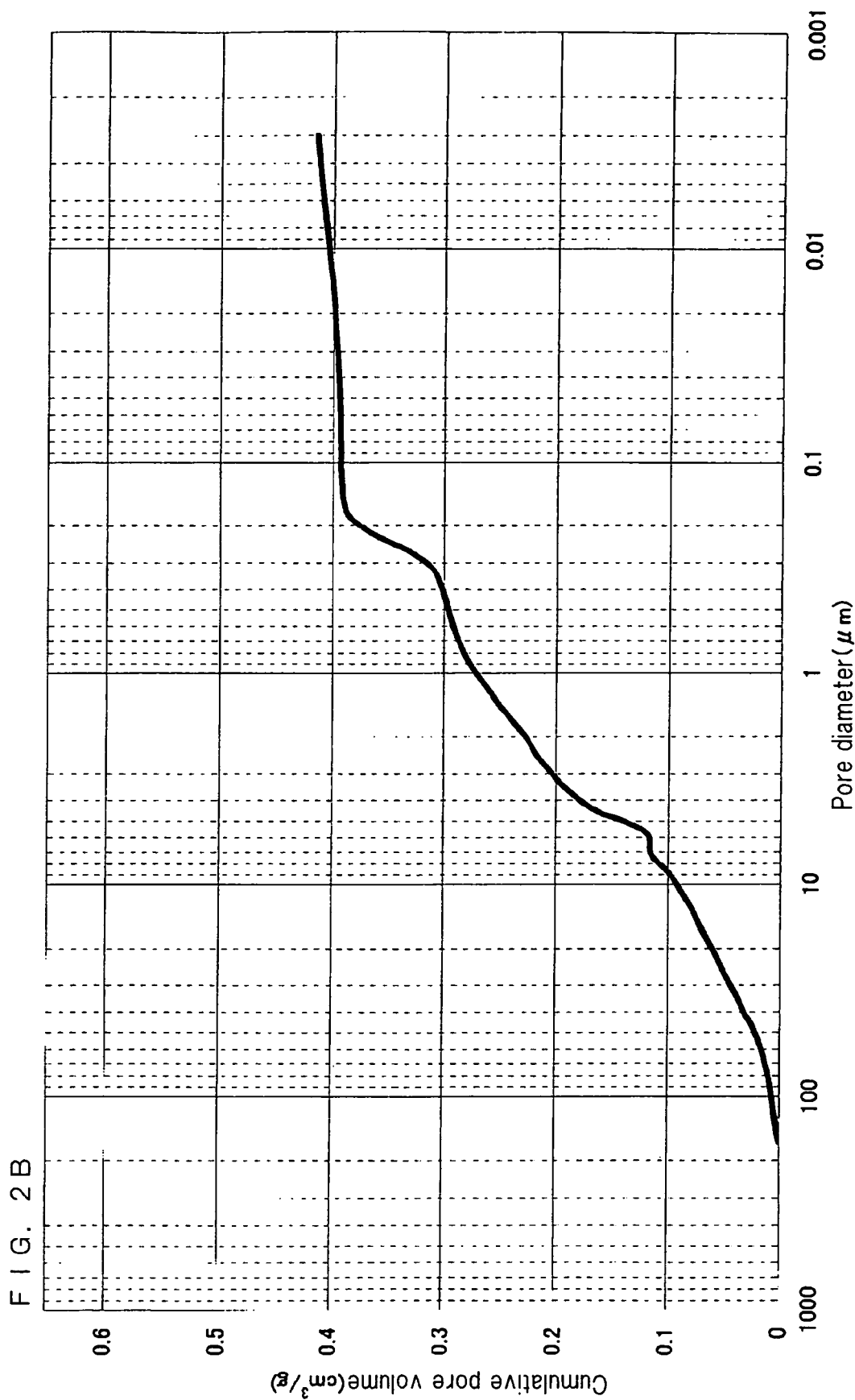

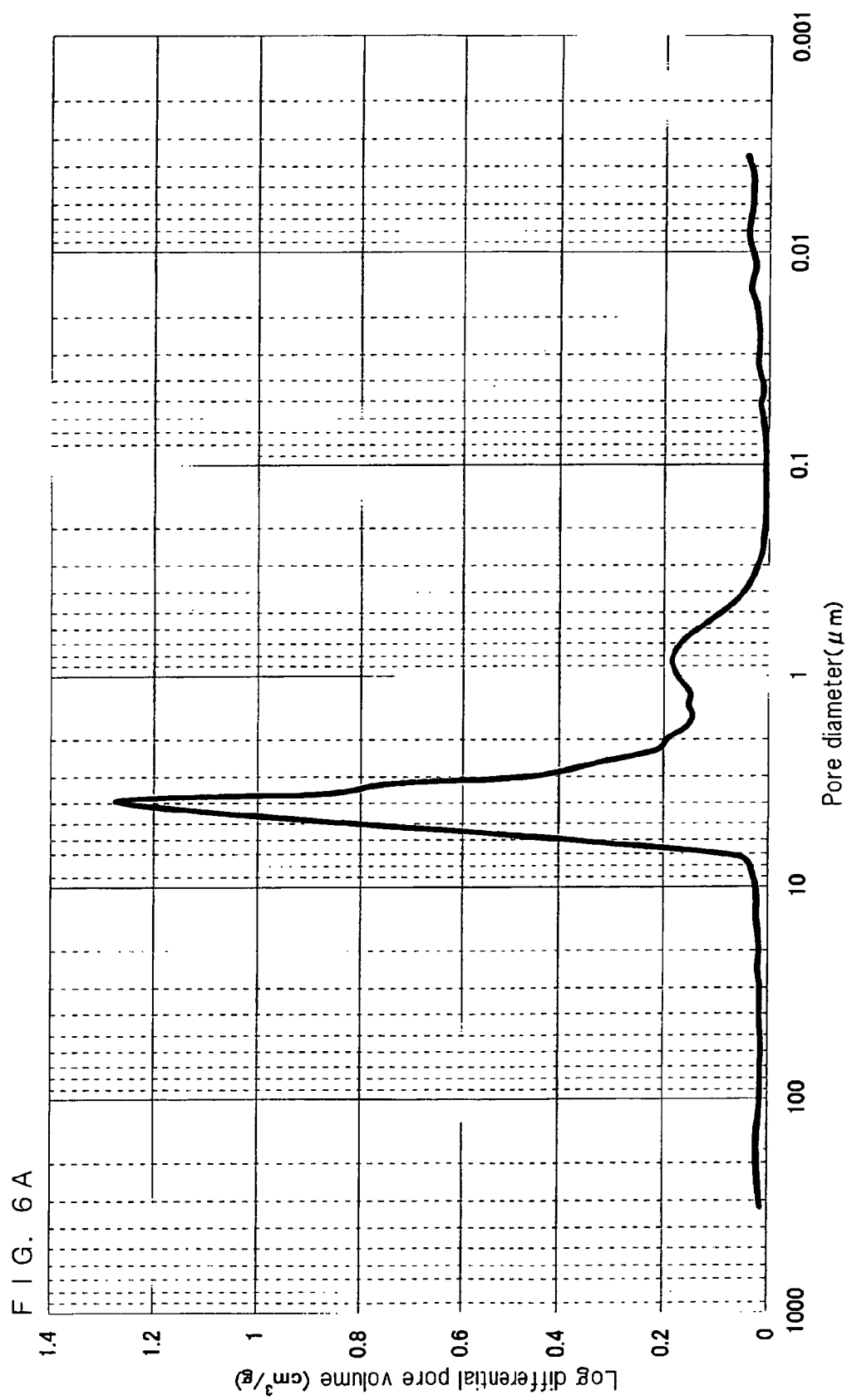

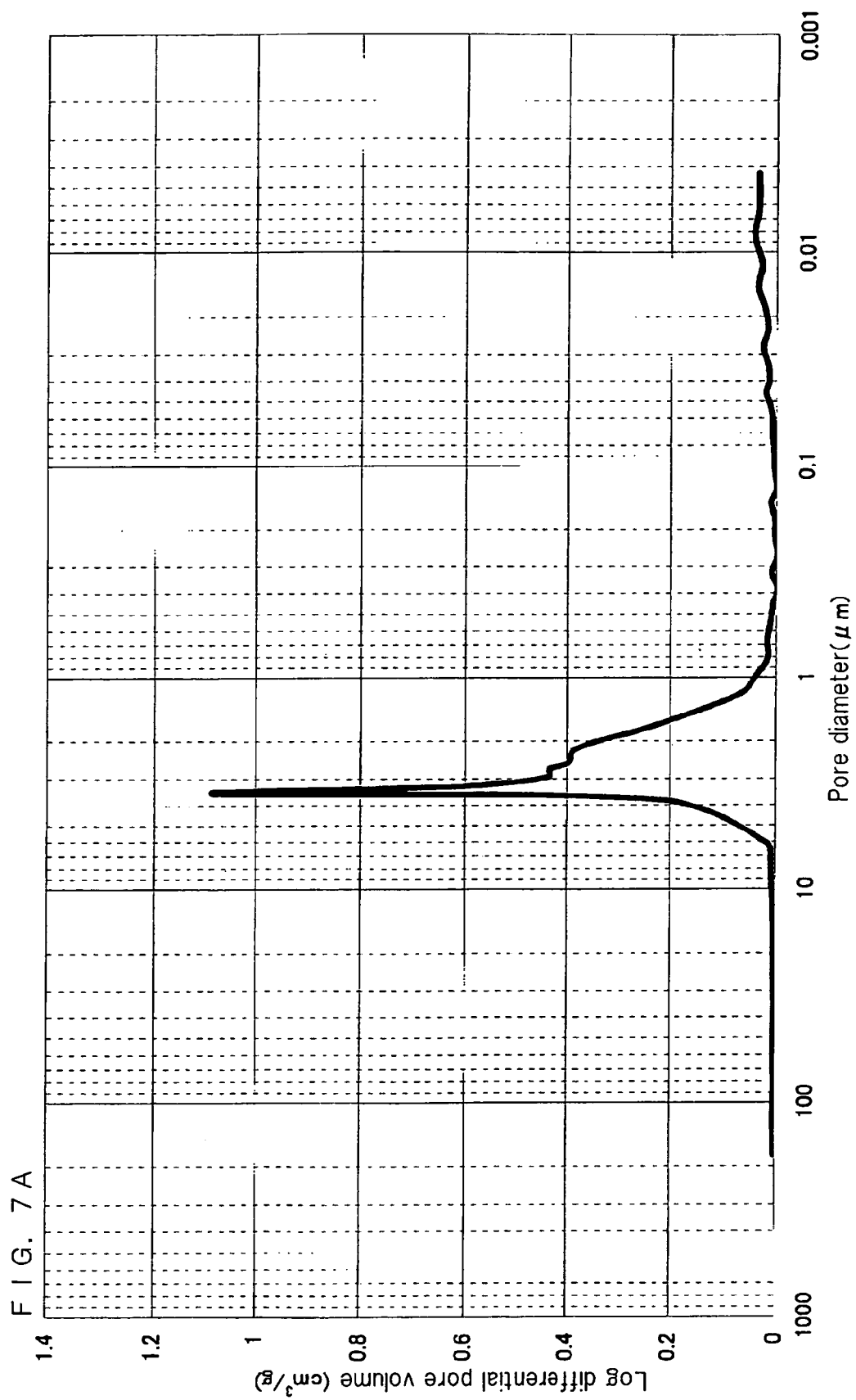

CATALYST FOR PRODUCTION OF ETHYLENE OXIDE AND METHOD FOR PRODUCTION OF ETHYLENE OXIDE

BACKGROUND OF THE INVENTION

1. Field of the Invention

This invention relates to a catalyst for the production of ethylene oxide and a method for the production of ethylene oxide, and in particular to a catalyst excellent in selectivity for ethylene oxide that enables ethylene oxide to be produced in a high selectivity, and a method for the production of ethylene oxide using this catalyst.

2. Description of Related Art

Industrial production of ethylene oxide by the catalytic vapor phase oxidation of ethylene with a molecular oxygen-containing gas in the presence of a silver catalyst is broadly conducted. Many technologies are proposed concerning the carrier, the supporting method, the reaction promoter and the like in relation to the silver catalyst to be used for the catalytic vapor phase oxidation.

For example, a carrier containing α-alumina as the main component and having a predetermined median pore diameter and a predetermined pore volume, and a catalyst using this carrier are disclosed in JP-A-2000-44331 as a technology for controlling properties of a carrier composing a catalyst. For another example, a technology for controlling the surface area and water absorption of a carrier so as to be at predetermined values and controlling the pore volume and pore diameter of a carrier so as to have a predetermined relation is disclosed in WO 03/072244 and WO 03/072246.

Although the catalytic activity, selectivity and catalyst life of a silver catalyst are already at a high level, these catalytic performance are still required to be improved. Taking selectivity as an example, the amount of the raw material, ethylene, to be used is remarkably saved leading to a marked economic effect by improving the selectivity by only 1%, because of a large production scale of ethylene oxide. Under these circumstances, development of a silver catalyst having higher performance has been an incessant research theme in the related technical field.

BRIEF SUMMARY OF THE INVENTION

The silver catalysts disclosed in the above patent publications, however, have still posed a problem of insufficient catalytic performance.

An object of this invention is, therefore, to provide a catalyst that enables ethylene oxide to be produced in a high selectivity and a method for the production of ethylene oxide using this catalyst.

We have found, after having intensively studied a way to solve the above problem, that a catalyst for the production of ethylene oxide that enables ethylene oxide to be produced in a high selectivity can be obtained by adopting a carrier containing α-alumina as the main component which has at least two peaks in the range of pore diameter of 0.01-100 μm and at least one peak of the above peaks is present in the range of pore diameter of 0.01-1.0 μm in the pore distribution measured by mercury porosimetry, as the carrier composing the catalyst, and completed this invention.

In other words, a aspect of this invention is a catalyst for the production of ethylene oxide, comprising: a carrier containing α-alumina as the main component which has at least two peaks in the range of pore diameter of 0.01-100 μm and at least one peak of the above peaks is present in the range of pore diameter of 0.01-1.0 μm in the pore distribution measured by mercury porosimetry; and a catalyst component is supported on the carrier, and a method for the production of ethylene oxide using this catalyst.

According to this invention, a catalyst that enables ethylene oxide to be produced in a high selectivity and a method for the production of ethylene oxide using this catalyst can be provided.

The above and other objects, features and advantages of this invention will become clear from the following description of the preferred embodiments.

BRIEF DESCRIPTION OF THE DRAWINGS

FIG. 2A is a graph showing the pore distribution (log differential pore volume) of carrier B used in Example 2.

FIG. 2B is a graph showing the pore distribution (cumulative pore volume) of carrier B used in Example 2.

FIG. 6A is a graph showing the pore distribution (log differential pore volume) of carrier F used in Control 2.

FIG. 7A is a graph showing the pore distribution (log differential pore volume) of carrier G used in Control 3.

DETAILED DESCRIPTION OF THE INVENTION

This invention is a catalyst for the production of ethylene oxide, comprising: a carrier containing α-alumina as the main component which has at least two peaks in the range of pore diameter of 0.01-100 μm and at least one peak of the above peaks is present in the range of pore diameter of 0.01-1.0 μm in the pore distribution measured by mercury porosimetry; and a catalyst component is supported on the carrier, and a method for the production of ethylene oxide using the catalyst. The catalyst for the production of ethylene oxide of this invention has excellent catalytic performance and enables ethylene oxide to be produced in a high selectivity for a long period (in an excellent catalyst life).

The other embodiment (shape of the carrier, specific embodiment of the catalyst components, and the like) of the catalyst for the production of ethylene oxide of this invention is not particularly limited, as long as the pore distribution of the carrier measured by mercury porosimetry shows the specified peaks as described above.

Figure 1A:
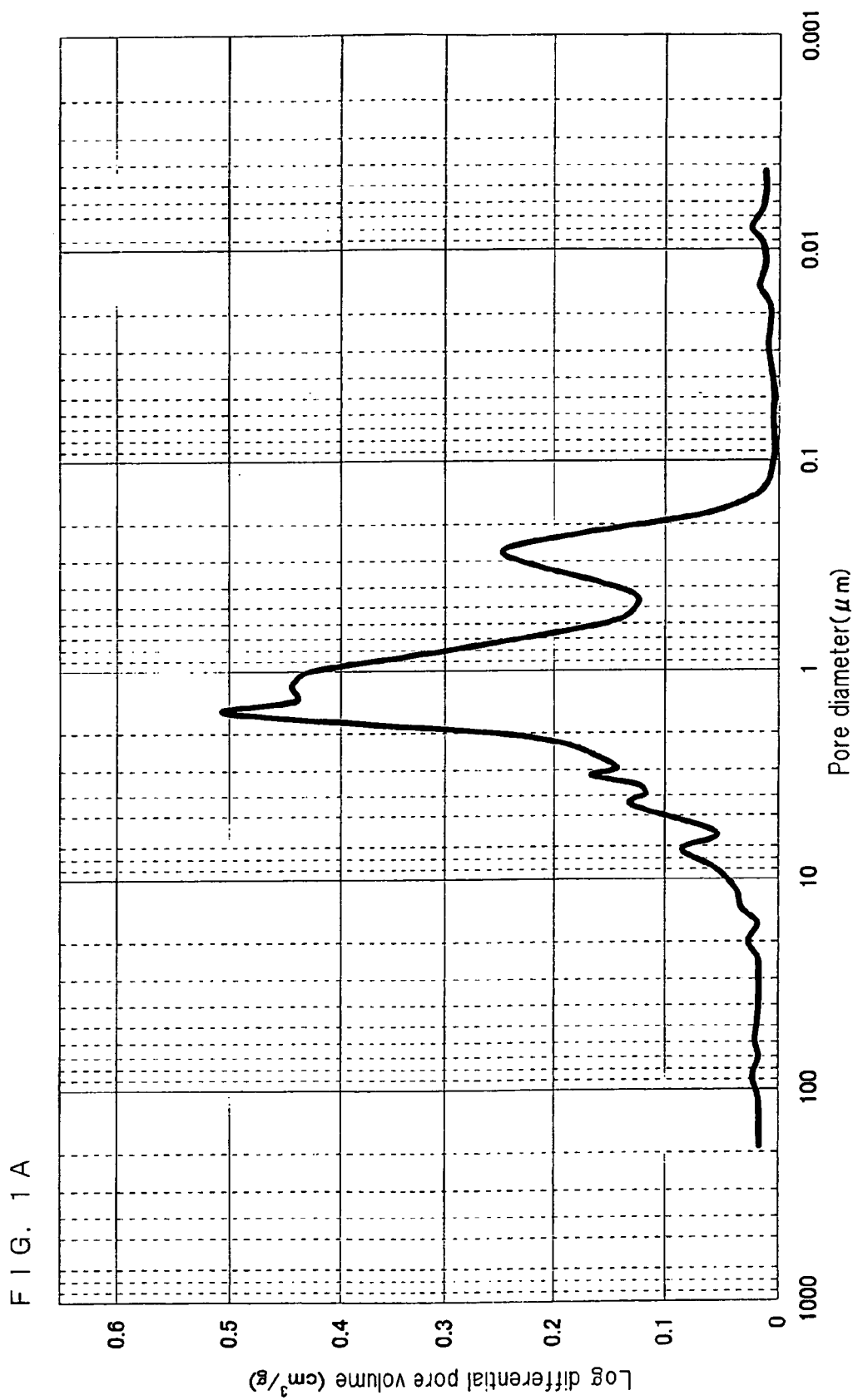
FIG. 1A is a graph showing the pore distribution (log differential pore volume) of carrier A used in Example 1.
Figure 1B:
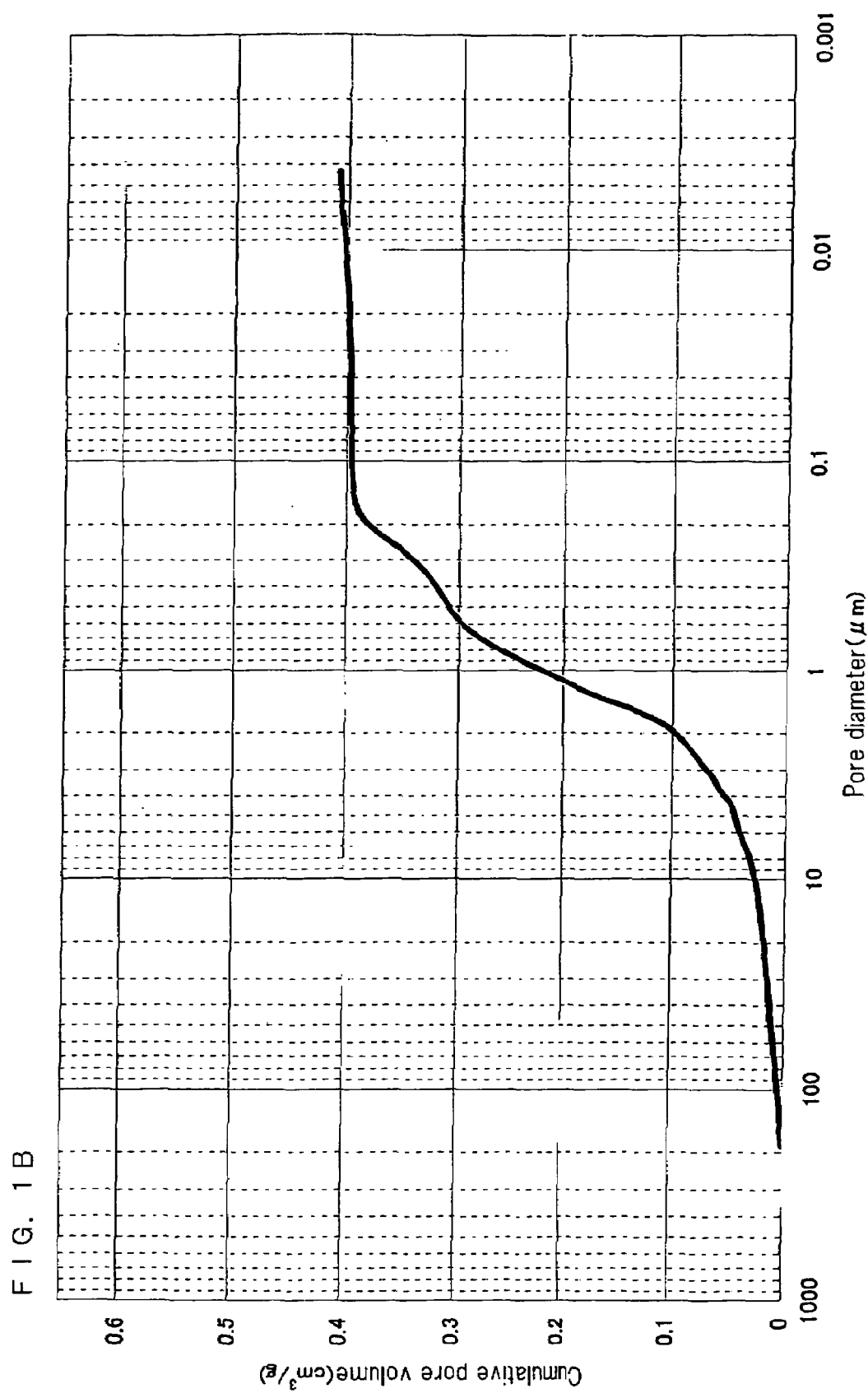
FIG. 1B is a graph showing the pore distribution (cumulative pore volume) of carrier A used in Example 1.

The pore distribution of a carrier is obtained by mercury porosimetry in this invention. It is assumed here that every pore is cylindrical, and the pore diameter and the pore volume are indicated by diameter D and V respectively. The log differential pore volume distribution is most frequently used to express a broad range of pore distribution and is obtained by plotting the value obtained by dividing the pore volume difference dV by the difference value of the logarithm of pore diameter d (log D) against the median pore diameter in each section. Incidentally, "difference pore volume dV" means an increment of pore volume between measuring points. For example, the axis of abscissa indicates the pore diameter (logarithm scale) and the axis of ordinate indicates the log differential pore volume as shown in FIG. 1A. In addition, the cumulative pore volume distribution is obtained by plotting the pore diameter in the axis of abscissa and the pore volume $\Sigma V$ in the axis of ordinate. For example, the axis of abscissa indicates the pore diameter (logarithm scale) and the axis of ordinate indicates the cumulative pore volume as shown in FIG. 1B. Incidentally, the procedure in the examples to be described later is adopted for the specific procedure of mercury porosimetry to obtain the pore distribution.

In the pore distribution obtained by mercury porosimetry, the peak indicates the one having the maximum value of a log differential pore volume of 0.2 cm$^3$/g or larger and does not include the one having the maximum value smaller than 0.2 cm$^3$/g.

In the pore distribution of a carrier to be used for the catalyst of this invention, at least two peaks are present in the range of pore diameter of 0.01-100 μm. At least one peak of the above at least two peaks is present in the range of pore diameter of 0.01-1.0 μm, preferably 0.04-0.8 μm, more preferably 0.1-0.5 μm and particularly preferably 0.2-0.4 μm. Preferably, at least one peak present in the range of 0.01-1.0 μm makes it easy to support a catalyst component in a fine and highly-dispersed state. In particular, a large specific surface area allows each finely-crushed or dispersed particle of a catalyst component to take a wider space, which represses sintering of silver and a decline of catalytic activity and selectivity. The catalyst for the production of ethylene oxide keeping excellent catalytic performance for a long period can be thus obtained.

A catalyst that enables ethylene oxide to be produced in a high selectivity can be obtained by adopting a carrier showing such a peak in the pore distribution.

The composition of the carrier is not particularly limited except that the carrier contains α-alumina as the main component. The description that a carrier "contains α-alumina as the main component" means that the content of the α-alumina in the carrier is 90 mass % or higher based on 100 mass % of the carrier. The content of α-alumina in the carrier is preferably 95 mass % or higher, more preferably 98 mass % or higher. Other composition of the carrier is not particularly limited as long as the carrier contains α-alumina as the main component. The carrier may contain an oxide of an alkali metal or an alkaline-earth metal and an oxide of a transition metal. The content of these oxides is not particularly limited, but the content of an oxide of an alkali metal or an alkaline-earth metal is preferably 0-5 mass %, more preferably 0.01-4 mass % in terms of the oxide. The content of an oxide of a transition metal is preferably 0-5 mass %, more preferably 0.01-3 mass % in terms of the oxide.

In addition, the carrier usually contains silica (silicon dioxide). The content of silica in a carrier is not particularly limited, but is preferably 0.01-10.0 mass %, more preferably 0.1-5.0 mass % and still more preferably 0.2-3.0 mass %.

Incidentally, the above composition of a carrier and the content of each component can be determined by fluorescent X-ray analysis.

The shape of a carrier is not particularly limited, but is ring-shaped, sphere-shaped, cylinder-shaped and pellet-shaped, and in addition may refer to conventionally known information as appropriate. The size (mean diameter) of a carrier is not particularly limited either, but is preferably 3-20 mm, more preferably 5-10 mm.

The particle diameter of α-alumina, which is a raw material of a carrier, is not particularly limited either, but the primary particle diameter of α-alumina is preferably 0.01-100 μm, more preferably 0.1-20 μm, still more preferably 0.5-10 μm and particularly preferably 1-5 μm and the secondary particle diameter of α-alumina is preferably 0.1-1,000 μm, more preferably 1-500 μm, still more preferably 10-200 μm and particularly preferably 30-100 μm.

The specific surface area of a carrier is not particularly limited either, but is preferably 0.03-10 m$^2$/g, more preferably 0.5-5.0 m$^2$/g and still more preferably 1.0-3.0 m$^2$/g. The specific surface area of a carrier of 0.03 m$^2$/g or larger allows the carrier to support a required amount of a catalyst component. The larger the specific surface area of a carrier is, the more easily a catalyst component is highly-dispersed on the carrier. In addition, a carrier with a larger specific surface area favorably gives a larger surface area of a catalyst component serving as an activity site of catalytic reaction. On the other hand, the specific surface area of a carrier of 10 m$^2$/g or smaller keeps the pore diameter of the carrier rather large and can repress sequential oxidation of ethylene oxide during the production of ethylene oxide using the produced catalyst. Incidentally, the value obtained by the procedure in the examples to be described later is adopted for the specific surface area of a carrier.

The pore volume of a carrier is not particularly limited either, but is preferably 0.2-0.6 cm$^3$/g, more preferably 0.3-0.5 cm$^3$/g and still more preferably 0.35-0.45 cm$^3$/g. The pore volume of a carrier of 0.2 cm$^3$/g or larger favorably makes it easier to support a catalyst component. On the other hand, the pore volume of a carrier of 0.6 cm$^3$/g or smaller favorably can give practical strength to the carrier. Incidentally, the value obtained by the procedure in the examples to be described later is adopted for the pore volume of a carrier.

A carrier having a ratio of the volume of the pore having a predetermined pore diameter to the above pore volume of a carrier in a predetermined range can give a catalyst for the production of ethylene oxide of more-excellent catalytic performance. Specifically, the pore having a pore diameter of 0.1-0.5 μm occupies preferably 5-50 vol %, more preferably 10-45 vol % and still more preferably 15-35 vol % and particularly preferably 19-25 vol % of the total pore volume.

The size of the pore of a carrier is not particularly limited either, but the median pore diameter is preferably 0.1-10 μm, more preferably 0.2-4.0 μm, still more preferably 0.3-3.0 μm and particularly preferably 0.4-1.5 μm. The median pore diameter of 0.1 μm or larger can repress sequential oxidation of ethylene oxide caused by retention of the product gas during the production of ethylene oxide. On the other hand, the median pore diameter of 10 μm or smaller can give practical strength to the carrier. Incidentally, the value obtained by the procedure in the examples to be described later is adopted for the median pore diameter.

The water absorption of a carrier is not particularly limited either, but is preferably 10-70%, more preferably 20-60% and still more preferably 30-50%. The water absorption of 10% or higher makes it easier to support a catalyst component. On the other hand, the water absorption of 70% or lower can give practical strength to the carrier. Incidentally, the value obtained by the procedure in the examples to be described later is adopted for the water absorption of a carrier.

The catalyst of this invention has a structure in which a catalyst component is supported on the above carrier. The specific embodiment of the catalyst component is not particularly limited, but may refer to conventionally known information as appropriate, and preferably silver is contained as an essential catalyst component. In addition to silver, a catalyst component to be generally used as a reaction promoter may be supported by a carrier. Typical examples of the reaction promoter include an alkali metal, specifically lithium, sodium, potassium, rubidium and cesium. Besides alkali metals, thallium, sulfur, chromium, molybdenum, tungsten, rhenium and the like can be also used as a reaction promoter. These reaction promoters may be used alone or in combination of two or more. Among these, cesium is favorably used as a reaction promoter.

The amount of silver or a reaction promoter to be supported is not particularly limited and may be an effective amount for the production of ethylene oxide. For example, in the case of silver, the amount to be supported is 1-30 mass %, preferably 5-20 mass % based on the mass of a catalyst for the production of ethylene oxide. The amount of a reaction promoter to be supported is usually 0.001-2 mass %, preferably 0.01-1 mass % and more preferably 0.01-0.7 mass % based on the mass of a catalyst for the production of ethylene oxide.

In particular, the optimum amount of a reaction promoter to be supported depends on properties of a carrier, combination of reaction promoters and the like. It is preferable, therefore, that after catalysts having various amounts of a reaction promoter to be supported are prepared in advance and subjected to performance evaluation, the amount of the reaction promoter to be supported showing the maximum performance is determined to prepare the catalyst having the amount of the reaction promoter showing the maximum performance supported. In the following examples and controls, a catalyst was prepared after the amount of a reaction promoter to be supported showing the maximum performance was thus determined in advance.

The catalyst for the production of ethylene oxide of this invention can be prepared according to a conventionally known production method for a catalyst for the production of ethylene oxide except that the above carrier is used.

It is known that the properties of a carrier can be controlled by adopting the following methods for preparing a carrier. Namely, 1) a method of adding a pore-forming agent of an optional size and amount to base powder containing α-alumina as the main component, 2) a method of blending at least two kinds of base powder of different properties at an optional mixing ratio, 3) a method of calcining a carrier at an optional temperature for an optional time, and a combined method of these methods are known. These methods for preparing a carrier is described in, for example, "Porous Materials Characterization, Production and Application" supervised by Yasushi Takeuchi, published by Fuji Technosystem Inc. (1999). In addition, JP-A-5 (1993)-329368, JP-A-2001-62291, JP-A-2002-136868, JP-B-2983740, JP-B-3256237, JP-B-3295433 and the like are available for reference.

One example of the procedure for producing the catalyst for the production of ethylene oxide of this invention using the above carrier will be described hereinafter, but the technical scope of this invention should be defined by the scope of claims and is not limited to the following procedure.

Firstly, a carrier is prepared. As the method for preparing a carrier is described above, the detail description will be omitted here.

On the other hand, a solution to be used for silver to be supported by a carrier is prepared. Specifically, a silver compound alone or a complexing agent for forming a silver complex or a reaction promoter as necessary is added into a solvent such as water.

The silver compound includes, for example, silver nitrate, silver carbonate, silver oxalate, silver acetate, silver propionate, silver lactate, silver citrate and silver neodecanoate. The complexing agent includes, for example, monoethanolamine, diethanolamine, triethanolamine, ethylenediamine and propylenediamine. These silver compounds and complexing agents may be used alone or in combination of two or more.

Secondly, the above-prepared carrier is impregnated with the above-obtained solution. In this step, a reaction promoter may be dissolved in the solution before the carrier is impregnated with the solution and be subjected to impregnation at the same time or may be supported after the silver is supported.

The impregnated carrier is then dried and calcined. Preferably, drying is conducted at 80-120° C. under an atmosphere of air, oxygen or an inert gas (for example, nitrogen). Preferably, calcination is conducted at 150-700° C., preferably 200-600° C. under an atmosphere of air, oxygen or an inert gas (for example, nitrogen). Calcination may be conducted in one step or two or more steps. The preferable condition for calcination includes a condition that the first step is conducted at 150-250° C. for 0.1-10 hours under an atmosphere of air and the second step is conducted at 250-450° C. for 0.1-10 hours under an atmosphere of air. More preferably, the third step of calcination is conducted at 450-700° C. for 0.1-10 hours under an atmosphere of an inert gas (for example, nitrogen, helium and argon) after the second step of calcination.

The second aspect of this invention is a method for the production of ethylene oxide comprising a step for the catalytic vapor phase oxidation of ethylene with a molecular oxygen-containing gas in the presence of the catalyst for the production of ethylene oxide of the first aspect of this invention.

The method for the production of ethylene oxide of the second aspect of this invention can be conducted according to an ordinary method except that the catalyst for the production of ethylene oxide of the first aspect of this invention is used as the catalyst.

For example, general conditions in industrial-scale production of a reaction temperature of 150-300° C., preferably 180-280° C., a reaction pressure of 2-40 kg/cm$^2$G, preferably 10-30 kg/cm$^2$G and a space velocity of 1,000-30,000 hr$^{-1}$ (STP), preferably 3,000-8,000 hr$^{-1}$ (STP) are adopted. The feed gas to be brought into contact with the catalyst is composed of ethylene of 0.5-40 vol %, oxygen of 3-10 vol %, carbon dioxide of 1-20 vol %, an inert gas such as nitrogen, argon and steam of the balance, containing lower hydrocarbons such as methane and ethane and further a halide such as ethylene dichloride and diphenyl chloride of 0.1-10 ppm by volume as a reaction inhibitor. The molecular oxygen-containing gas to be used in the production method of this invention includes air, oxygen and enriched air.

EXAMPLES

The effect of this invention will be described using the following examples and controls. However, the technical scope of this invention is not limited to only the following examples. Incidentally, various parameters were measured by the following procedures in the examples.

<Measurement of Pore Distribution/Pore Volume/Median Pore Diameter of a Carrier>

These properties were measured by mercury porosimetry. Specifically, the sample of a carrier deaerated at 200° C. for at least 30 minutes was subjected to measurement under a pressure range of 1.0-60,000 psia and at 60 measurement points using Autopore III9420W (made by Shimadzu Corporation) to obtain pore distribution, pore volume and median pore diameter.

<Measurement of Content of Silica in a Carrier>

The content of silica was measured by fluorescent X-ray analysis.

<Measurement of Specific Surface Area of a Carrier>

About 0.2 g of the sample obtained by crushing a carrier and classified into a particle diameter of 0.85-1.2 mm was precisely weighed. The weighed sample was deaerated at 200° C. for at least 30 minutes and subjected to measurement by the BET (Brunauer-Emmet-Teller) method.

<Measurement of Water Absorption of a Carrier>

The water absorption was measured by the following procedures in accordance with the method described in the Japanese Industrial Standards (JIS R 2205 (1998)).

a) The carrier before crushing was put in a drier kept at 120° C. The weight of the carrier after becoming unchanged was measured (dry sample weight: W1 (g)).

b) The carrier weighed in the above a) was immersed in water, boiled for 30 minutes or longer and then cooled in water at room temperature to obtain a sample saturated with water.

c) The sample saturated with water obtained in the above b) was taken out of water, deprived of water droplets by swiftly wiping the surface with a wet cloth and then weighed (weight of sample saturated with water: W2 (g)).

d) The water absorption was calculated by Expression 1 below using above obtained W1 and W2.

$$\text{Water absorption (\%)} = \frac{W2 - W1}{W1} \times 100 \quad \text{[Expression 1]}$$

Example 1

4 L of a carrier (8 mm ring, bulk density: 0.70 g/mL, water absorption: 39.4%, content of α-alumina: 99.1 mass %) containing α-alumina as the main component was boiled three times each for 30 minutes or longer in 4 L of distilled water. The carrier was then dried well in a drier kept at 120° C. to obtain carrier A. The pore distribution of carrier A is shown (FIG. 1A: log differential pore volume vs. pore diameter, FIG. 1B: cumulative pore volume vs. pore diameter). As shown in FIG. 1A, in the pore distribution of carrier A, three peaks are present in the range of pore diameter of 0.01-100 μm (in more detail, in the range of 0.1-2.0 μm) and one peak is present in the range of pore diameter of 0.01-1.0 μm (in more detail, in the range of 0.1-0.5 μm).

On the other hand, 100 mL of water and a solution of 4.0 g of cesium nitrate dissolved in 250 mL of water was added into an aqueous slurry containing 520 g of silver oxalate (water content in the aqueous slurry: 150 g) and the slurry was made muddy. 250 mL of ethylenediamine was then added into this solution and stirred well to prepare an impregnation solution.

2,000 g of carrier A heated in advance up to about 100° C. was impregnated in the obtained impregnation solution. Subsequently, the carrier was subjected to heating, concentrating and drying and then activating at 400° C. for 20 minutes in airflow to obtain a catalyst precursor.

The obtained catalyst precursor was packed in a sealed container made of stainless steel to which an inert gas can be introduced from the outside, and subjected to heat treatment for 3 hours in an electric furnace while feeding nitrogen gas and keeping the catalyst layer temperature at 530° C., to prepare catalyst A for the production of ethylene oxide.

Example 2

Catalyst B for the production of ethylene oxide was prepared in accordance with the similar procedure as in above Example 1, except that carrier B having the pore distribution shown in FIG. 2A and FIG. 2B was used and the amount of cesium nitrate to be added was altered to 7.3 g.

Incidentally, as shown in FIG. 2A, in the pore distribution of carrier B, two peaks are present in the range of pore diameter of 0.01-100 μm (in more detail, in the range of 0.1-10.0 μm) and one peak is present in the range of pore diameter of 0.01-1.0 μm (in more detail, in the range of 0.1-0.5 μm).

Example 3

Figure 3A:
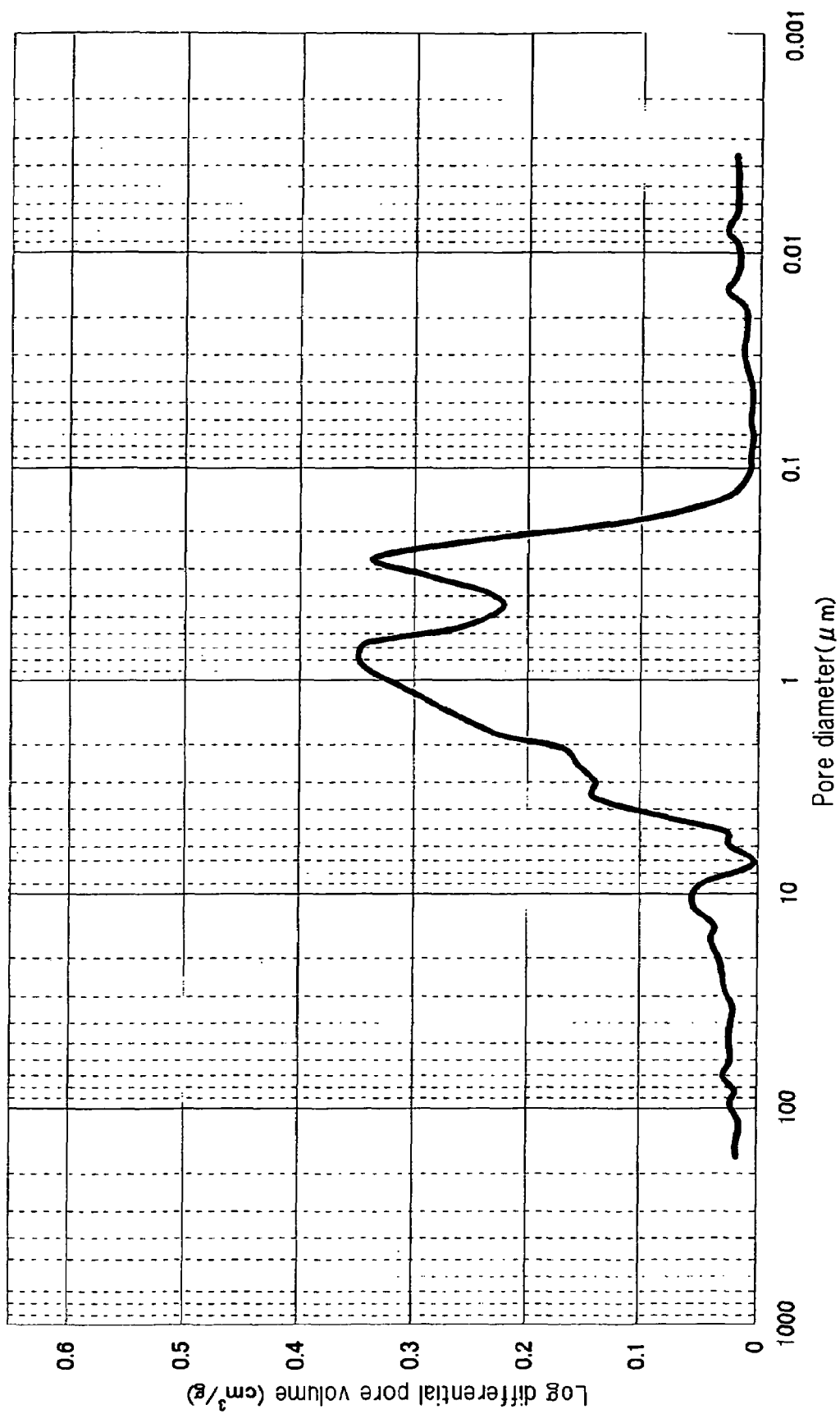
FIG. 3A is a graph showing the pore distribution (log differential pore volume) of carrier C used in Example 3.
Figure 3B:
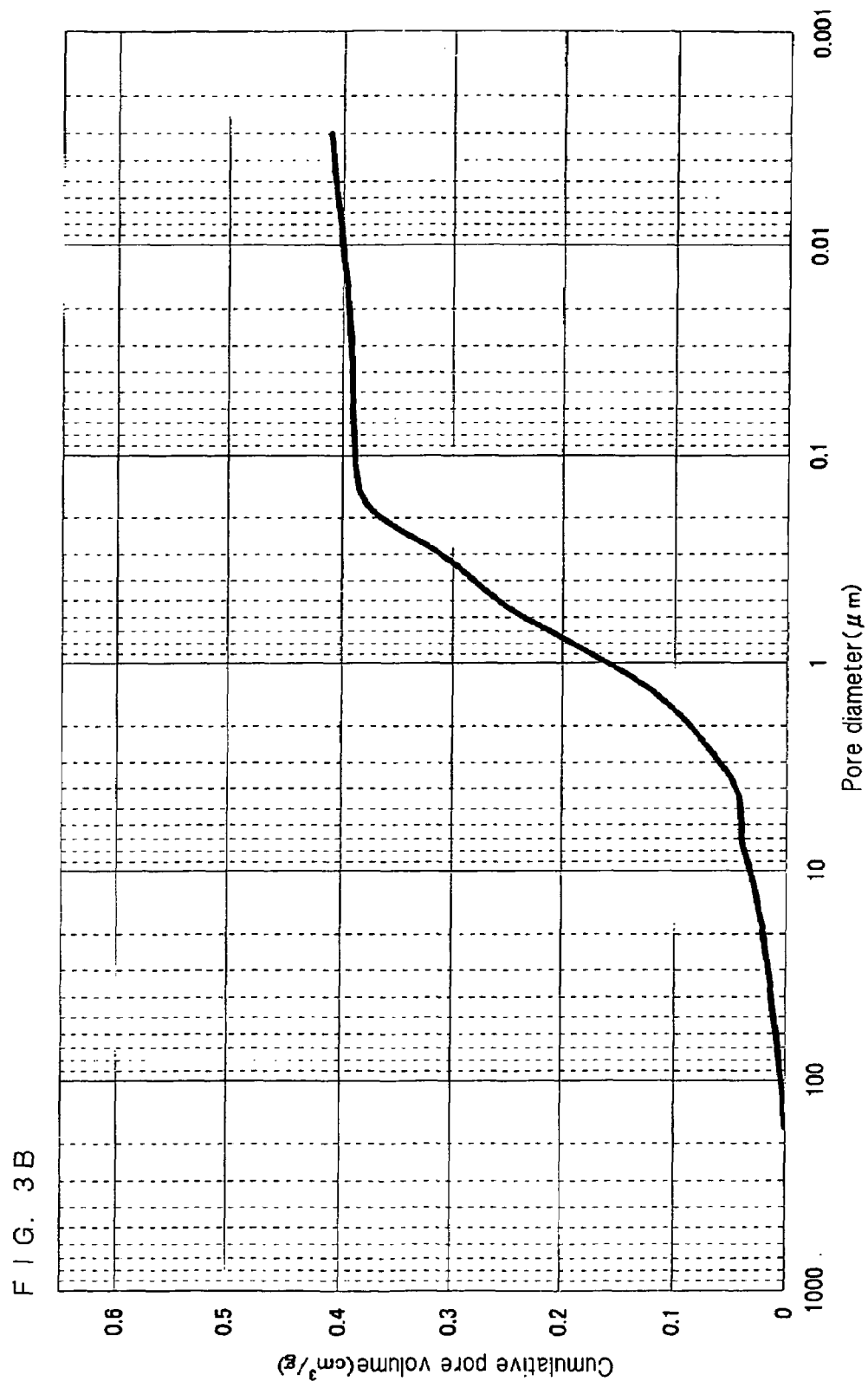
FIG. 3B is a graph showing the pore distribution (cumulative pore volume) of carrier C used in Example 3.

Catalyst C for the production of ethylene oxide was prepared in accordance with the similar procedure as in above Example 1, except that carrier C having the pore distribution shown in FIG. 3A and FIG. 3B was used and the amount of cesium nitrate to be added was altered to 4.7 g.

As shown in FIG. 3A, in the pore distribution of carrier C, two peaks are present in the range of pore diameter of 0.01-1.0 μm, and in more detail, one peak is present in the range of pore diameter of 0.1-0.5 μm.

Example 4

Figure 4A:
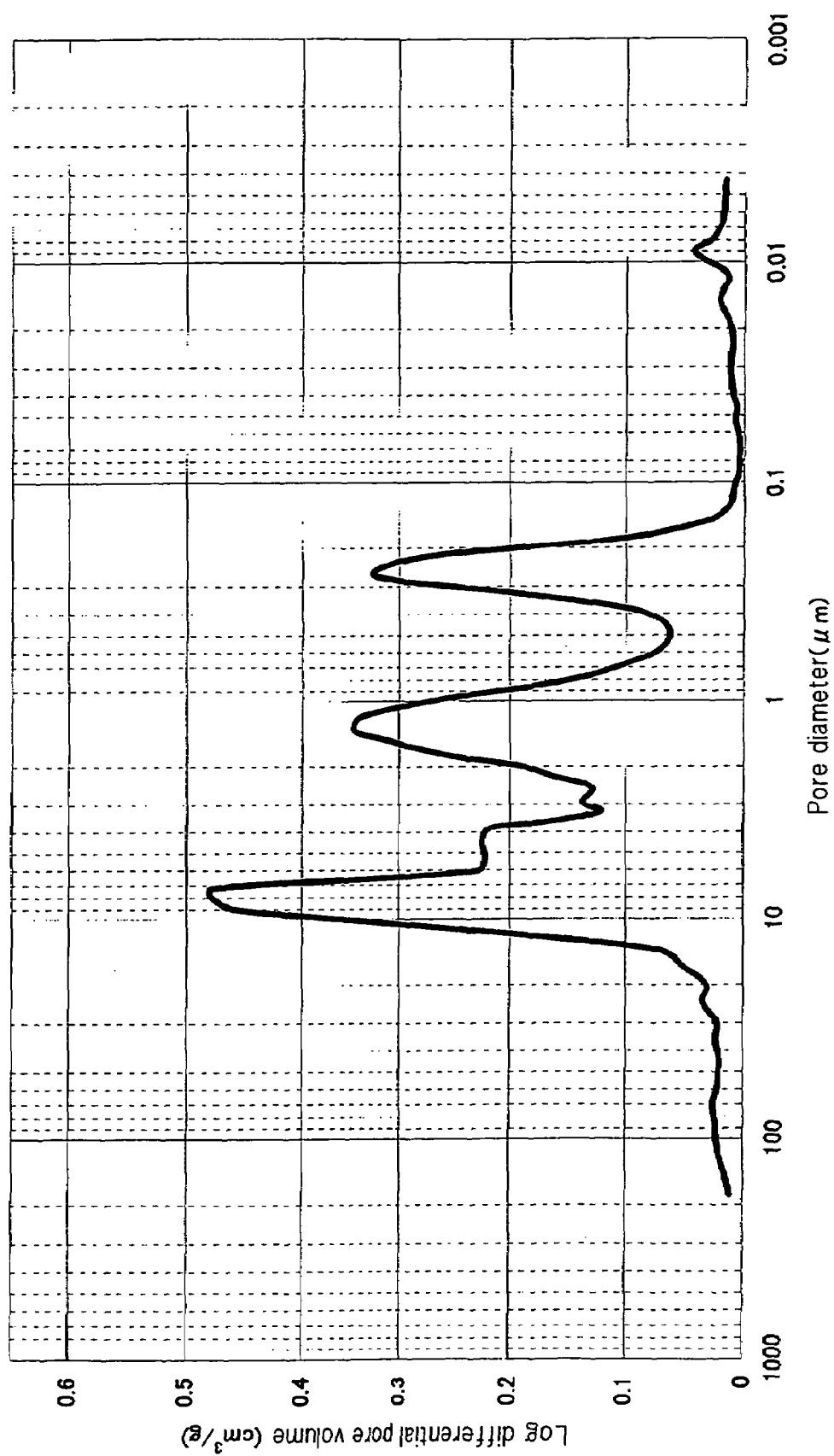
FIG. 4A is a graph showing the pore distribution (log differential pore volume) of carrier D used in Example 4.
Figure 4B:
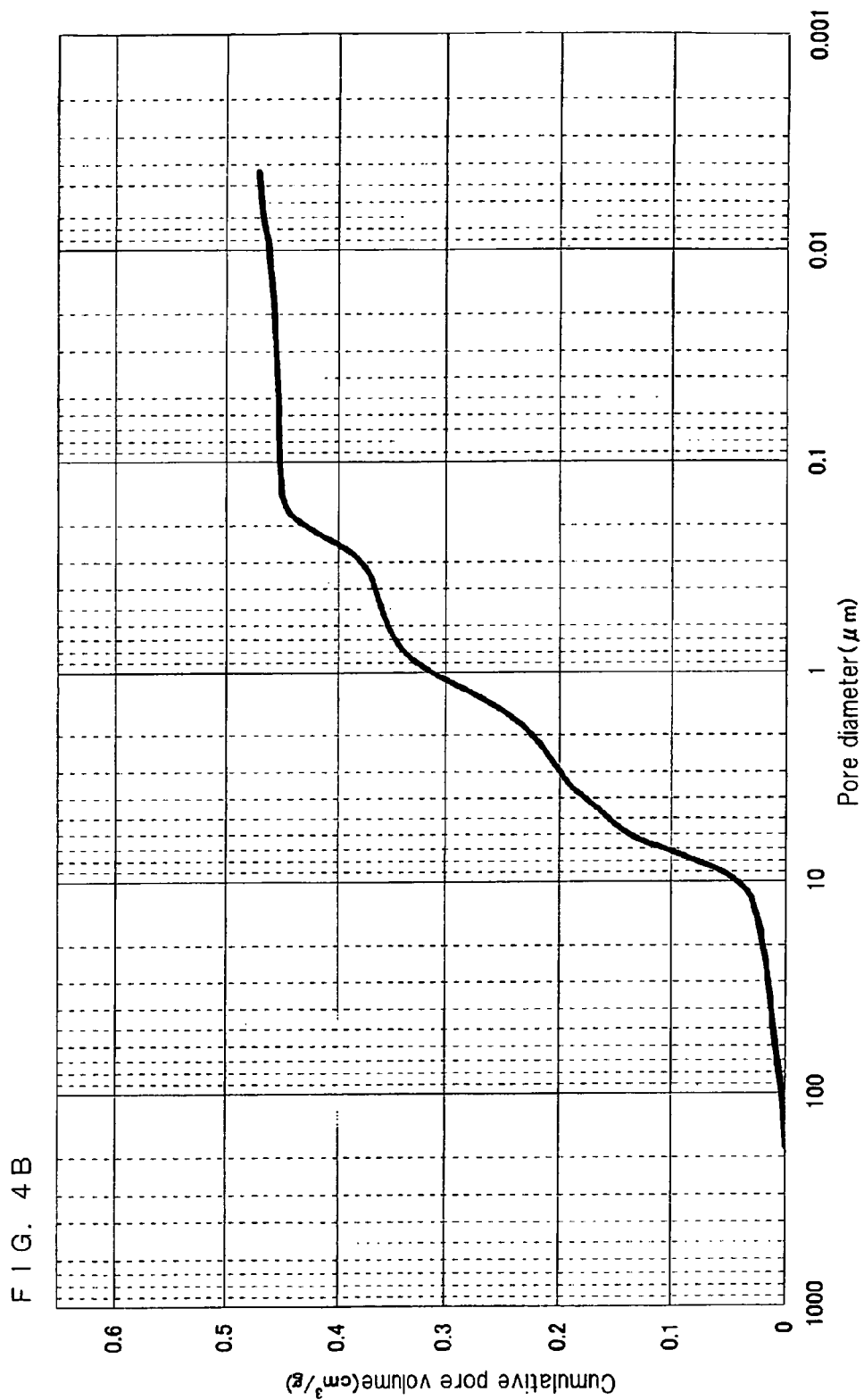
FIG. 4B is a graph showing the pore distribution (cumulative pore volume) of carrier D used in Example 4.

Catalyst D for the production of ethylene oxide was prepared in accordance with the similar procedure as in above Example 1, except that carrier D having the pore distribution shown in FIG. 4A and FIG. 4B was used.

As shown in FIG. 4A, in the pore distribution of carrier D, three peaks are present in the range of pore diameter of 0.01-100 μm (in more detail, in the range of 0.1-10.0 μm) and one peak is present in the range of pore diameter of 0.01-1.0 μm (in more detail, in the range of 0.1-0.5 μm).

(Control 1)

Figure 5A:
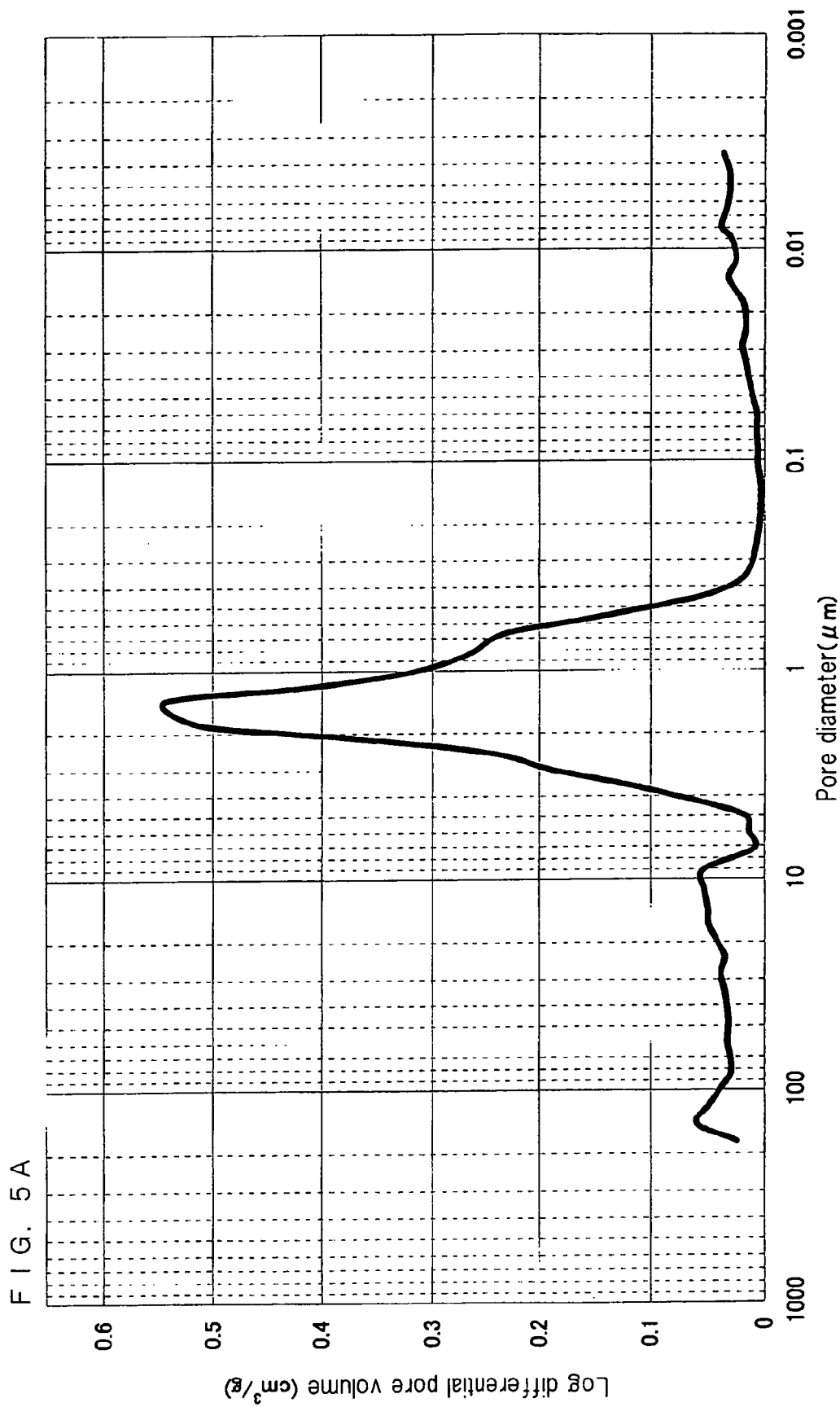
FIG. 5A is a graph showing the pore distribution (log differential pore volume) of carrier E used in Control 1.
Figure 5B:
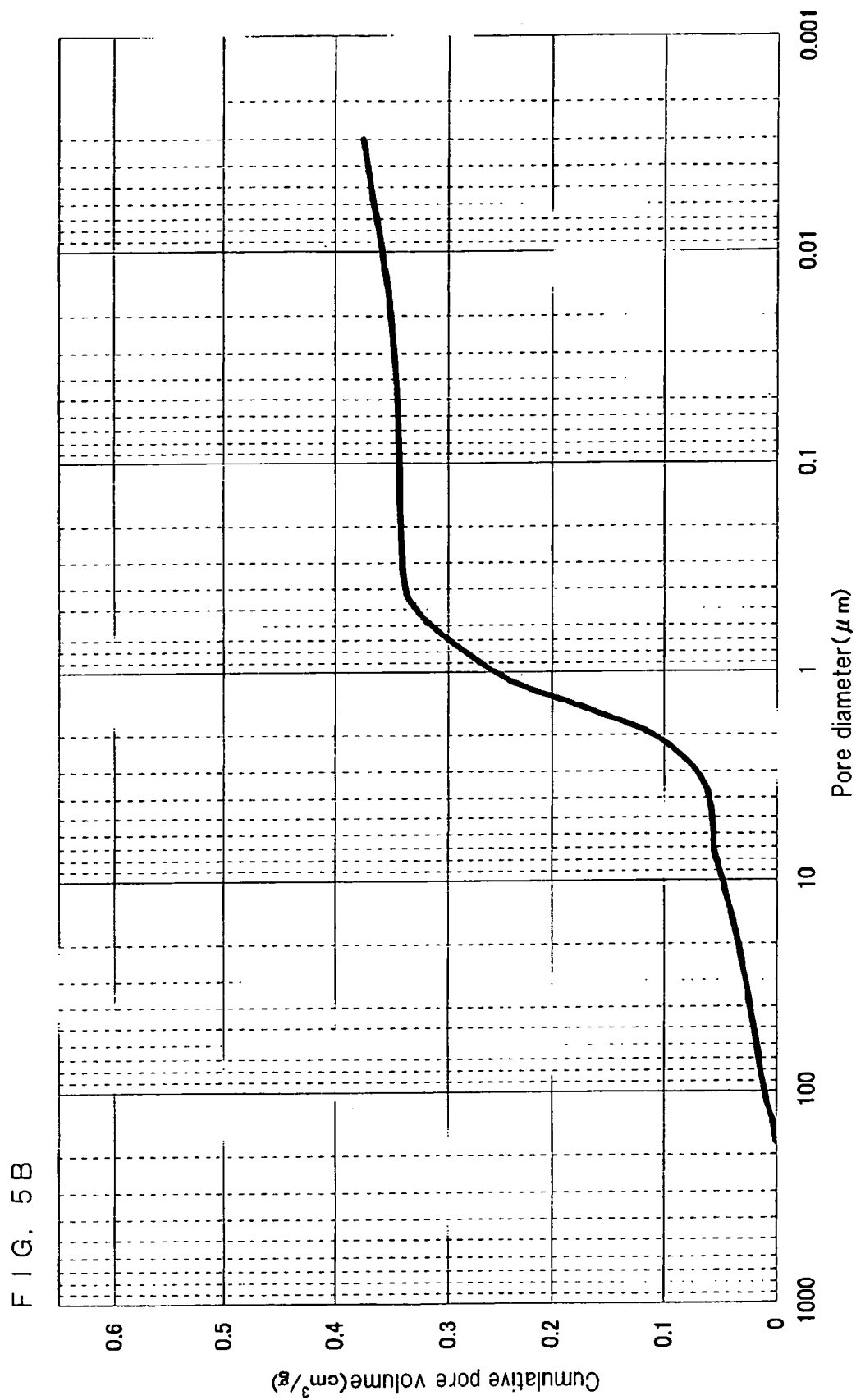
FIG. 5B is a graph showing the pore distribution (cumulative pore volume) of carrier E used in Control 1.

Catalyst E for the production of ethylene oxide was prepared in accordance with the similar procedure as in above Example 1, except that carrier E having the pore distribution shown in FIG. 5A and FIG. 5B was used and the amount of cesium nitrate to be added was altered to 2.7 g.

(Control 2)

Figure 6B:
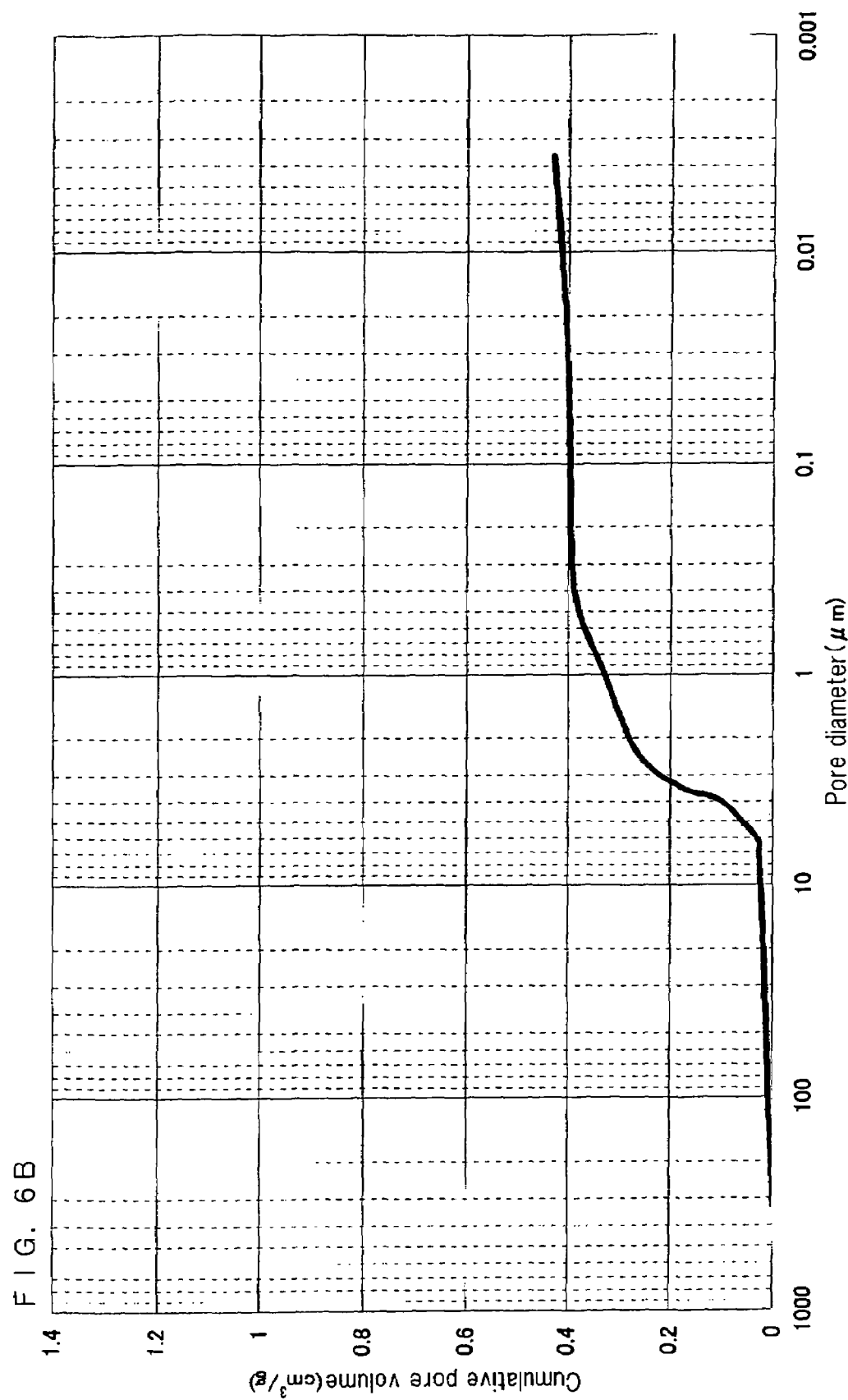
FIG. 6B is a graph showing the pore distribution (cumulative pore volume) of carrier F used in Control 2.

Catalyst F for the production of ethylene oxide was prepared in accordance with the similar procedure as in above Example 1, except that carrier F having the pore distribution shown in FIG. 6A and FIG. 6B was used and the amount of cesium nitrate to be added was altered to 2.7 g.

(Control 3)

Figure 7B:
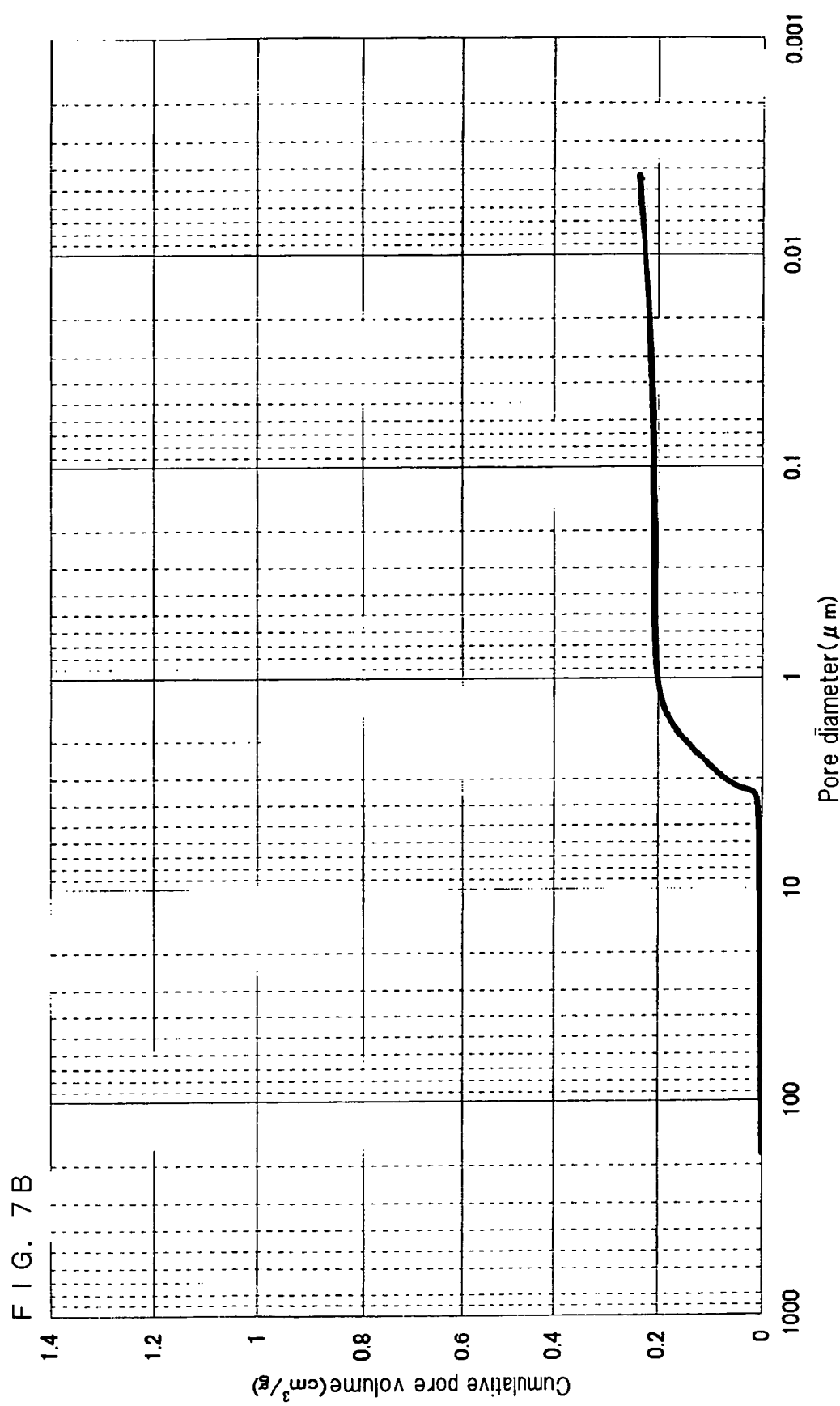
FIG. 7B is a graph showing the pore distribution (cumulative pore volume) of carrier G used in Control 3.

Catalyst G for the production of ethylene oxide was prepared in accordance with the similar procedure as in above Example 1, except that carrier G having the pore distribution shown in FIG. 7A and FIG. 7B was used and the amount of cesium nitrate to be added was altered to 1.5 g. Catalyst G was poor in performance and burned out before the conversion of ethylene reached 10% giving no result.

<Measurement of Conversion/Selectivity of a Catalyst>

The catalyst obtained in each example and each control was packed in an external-heating type double-pipe reactor made of stainless steel having an inside diameter of 25 mm and a length 7,500 mm to form a packed bed. Subsequently, a mixed gas composed of 21 vol % of ethylene, 7 vol % of oxygen, 7 vol % of carbon dioxide, the balance of methane, nitrogen, argon and ethane (methane: 52 vol %, nitrogen: 0.8 vol %, argon: 12 vol % and ethane: 0.2 vol %) and further containing 2 ppm of ethylene dichloride was introduced into the above packed bed to produce ethylene oxide under the conditions of a reaction pressure of 20 kg/cm$^2$G and a space velocity of 6,000 hr$^{-1}$. The conversion (Expression 2) and the selectivity (Expression 3) in ethylene oxide production were calculated in accordance with following Expression 2 and Expression 3 respectively. The results are shown in Table 1.

TABLE 1

| | | | Example | | | | Control | | | | | |
|---|---|---|---|---|---|---|---|---|---|---|---|---|
| | | | 1 | 2 | 3 | 4 | 1 | 2 | 3 | 4 | 5 | 6 |
| | Carrier | | A | B | C | D | E | F | G | H | I | J |
| Property | Water absorption | % | 39.4 | 42.2 | 41.5 | 46.4 | 39.5 | 39.1 | 25.0 | 32.6 | 25.0 | 53.4 |
| | Specific surface area | m$^2$/g | 1.6 | 1.2 | 2.1 | 1.6 | 0.8 | 0.8 | 0.2 | 0.3 | 0.3 | 0.8 |
| | Silica content | mass % | 0.7 | 2.5 | 0.7 | 0.7 | 0.7 | 0.7 | 0.3 | 5.6 | 0.3 | 0.1 |
| | Pore volume | cm$^3$/g | 0.41 | 0.41 | 0.41 | 0.47 | 0.38 | 0.43 | 0.24 | 0.34 | 0.24 | 0.53 |
| | Pore volume (0.1-0.5 μm) | % | 21.42 | 23.14 | 32.27 | 19.71 | 4.29 | 4.19 | 0.80 | 0.26 | 1.03 | 3.63 |
| | Median pore diameter | μm | 1.05 | 2.75 | 0.78 | 1.70 | 1.45 | 3.07 | 2.29 | 5.38 | 1.99 | 3.19 |
| Peak | Number | | 3 | 2 | 2 | 3 | 1 | 1 | 1 | 2 | 2 | 2 |
| | Location (μm) | 0.1-1.0 | ○ | ○ | ○ × 2 | ○ | — | — | — | — | — | — |
| | | 1.0-3.0 | ○ × 2 | — | — | ○ | ○ | — | — | ○ | ○ | ○ |
| | | 3.0-12 | — | ○ | — | ○ | — | ○ | ○ | ○ | ○ | ○ |
| Catalytic performance | Selectivity | % | 82.6 | 82.2 | 82.3 | 82.3 | 81.1 | 81.2 | reaction stopped | 80.8 | reaction stopped | 78.9 |
| | Conversion | % | 10 | 10 | 10 | 10 | 10 | 10 | — | 10 | — | 10 |
| | Reaction temperature | °C. | 232 | 233 | 235 | 230 | 229 | 232 | — | 239 | — | 247 |

$$\text{Conversion (\%)} = \frac{\text{Number of moles of reacted ethylene}}{\text{Number of moles of ethylene in feed gas}} \times 100 \quad \text{[Expression 2]}$$

$$\text{Selectivity (\%)} = \frac{\text{Number of moles of ethylene converted to ethylene oxide}}{\text{Number of moles of reacted ethylene}} \times 100 \quad \text{[Expression 3]}$$

(Control 4)

Figure 8A:
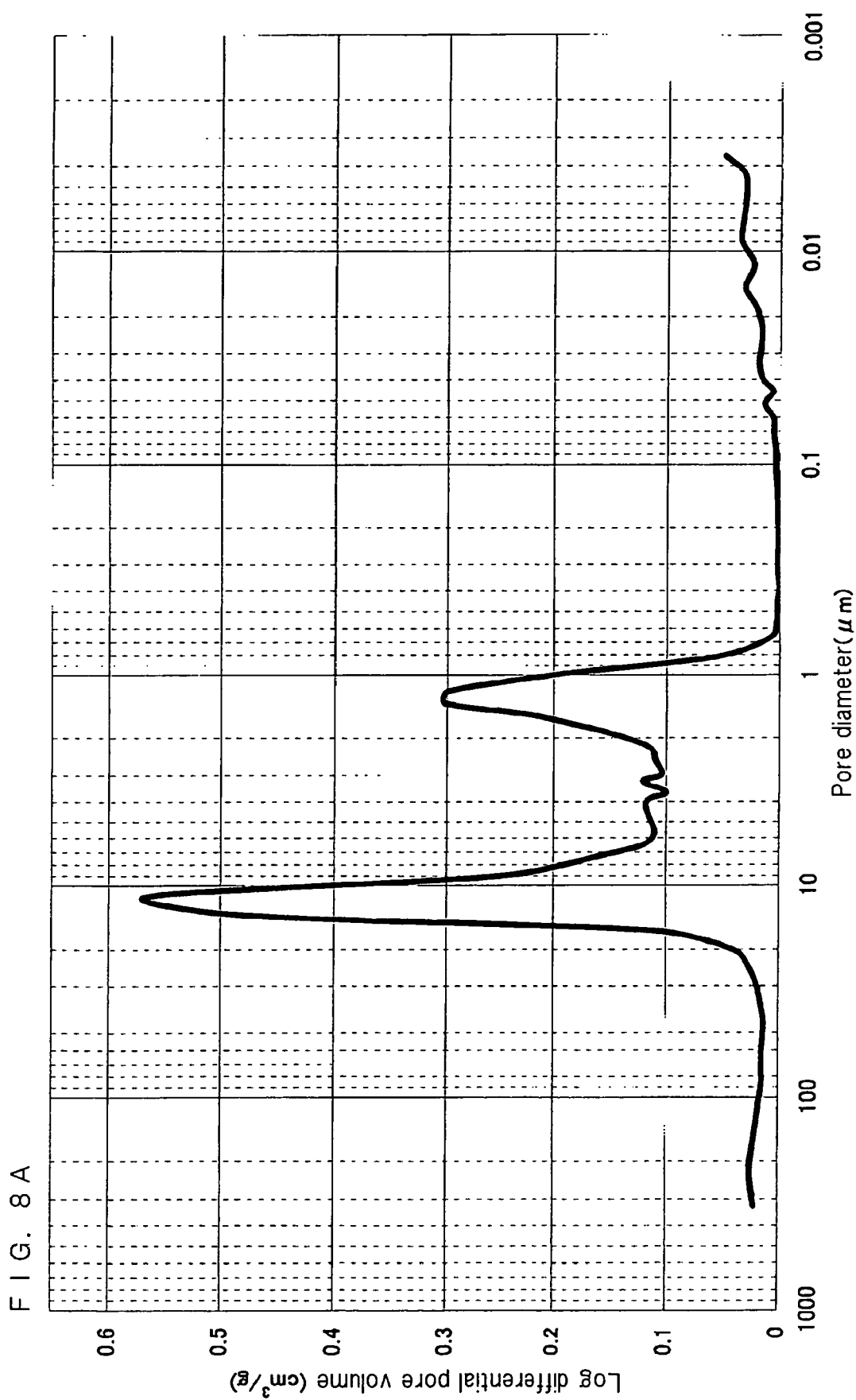
FIG. 8A is a graph showing the pore distribution (log differential pore volume) of carrier H used in Control 4.
Figure 8B:
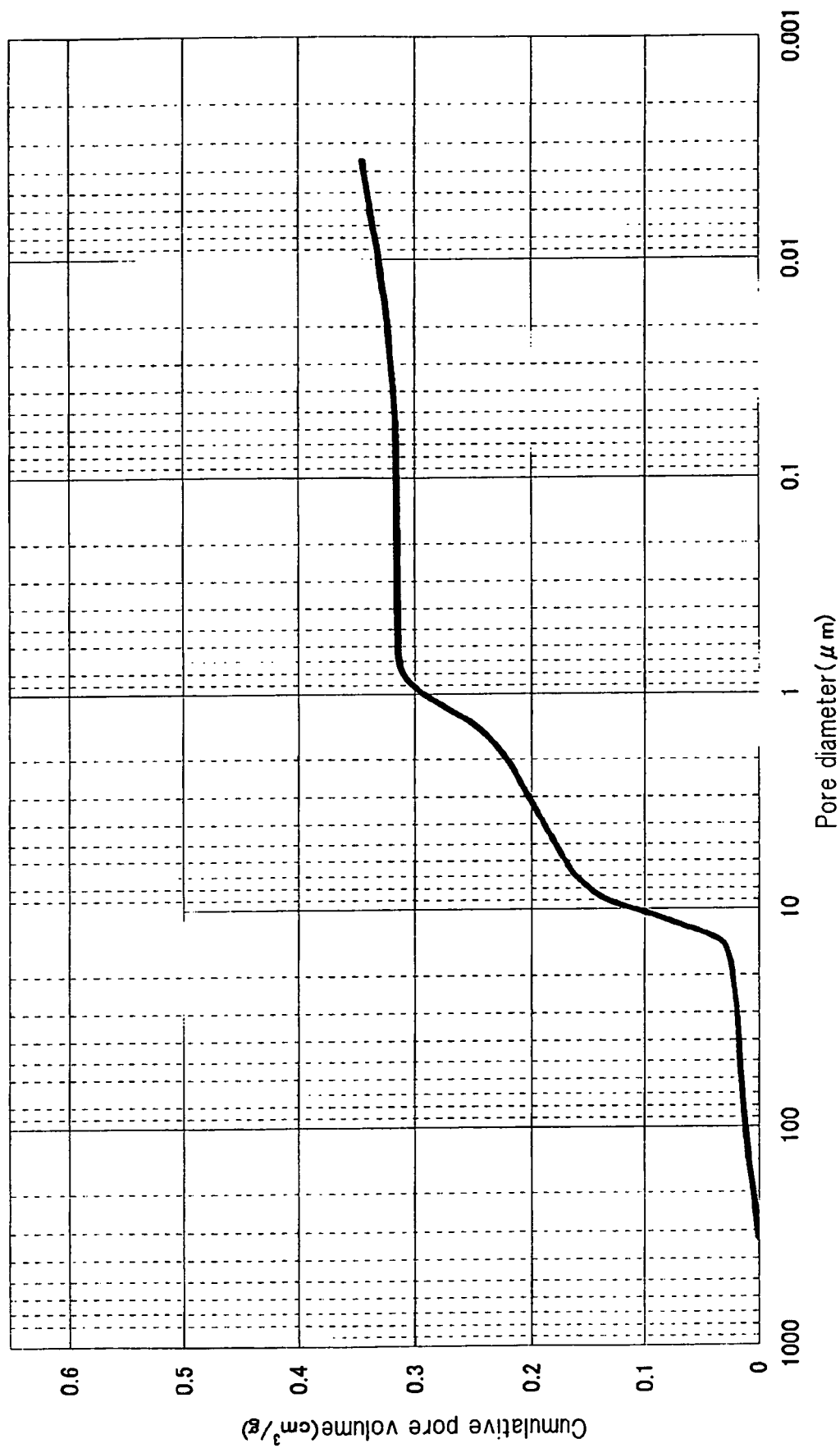
FIG. 8B is a graph showing the pore distribution (cumulative pore volume) of carrier H used in Control 4.

Catalyst H for the production of ethylene oxide was prepared in accordance with the similar procedure as in above Example 1, except that carrier H having the pore distribution shown in FIG. 8A and FIG. 8B was used and the amount of cesium nitrate to be added was altered to 2.2 g.

(Control 5)

Figure 9A:
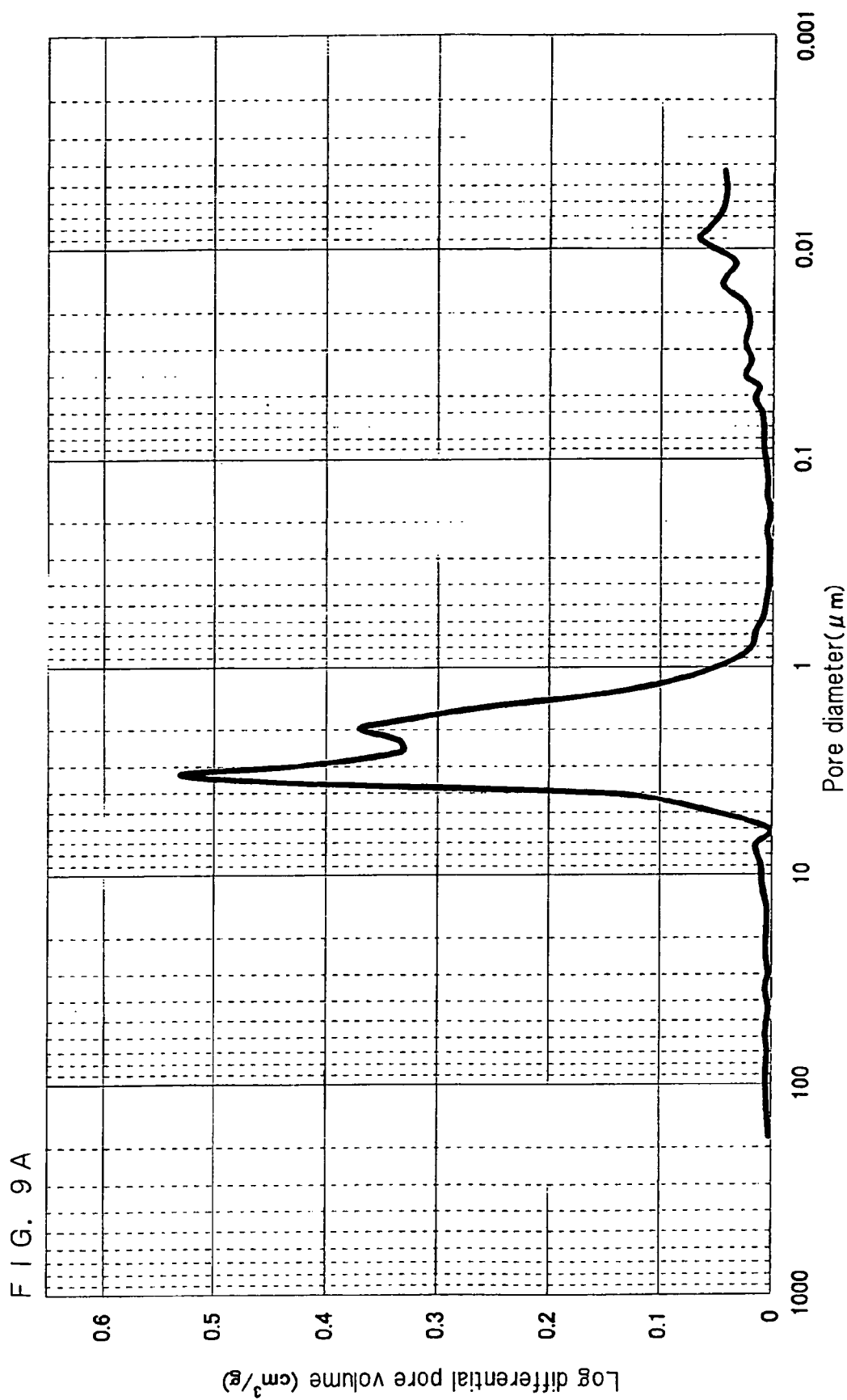
FIG. 9A is a graph showing the pore distribution (log differential pore volume) of carrier I used in Control 5.
Figure 9B:
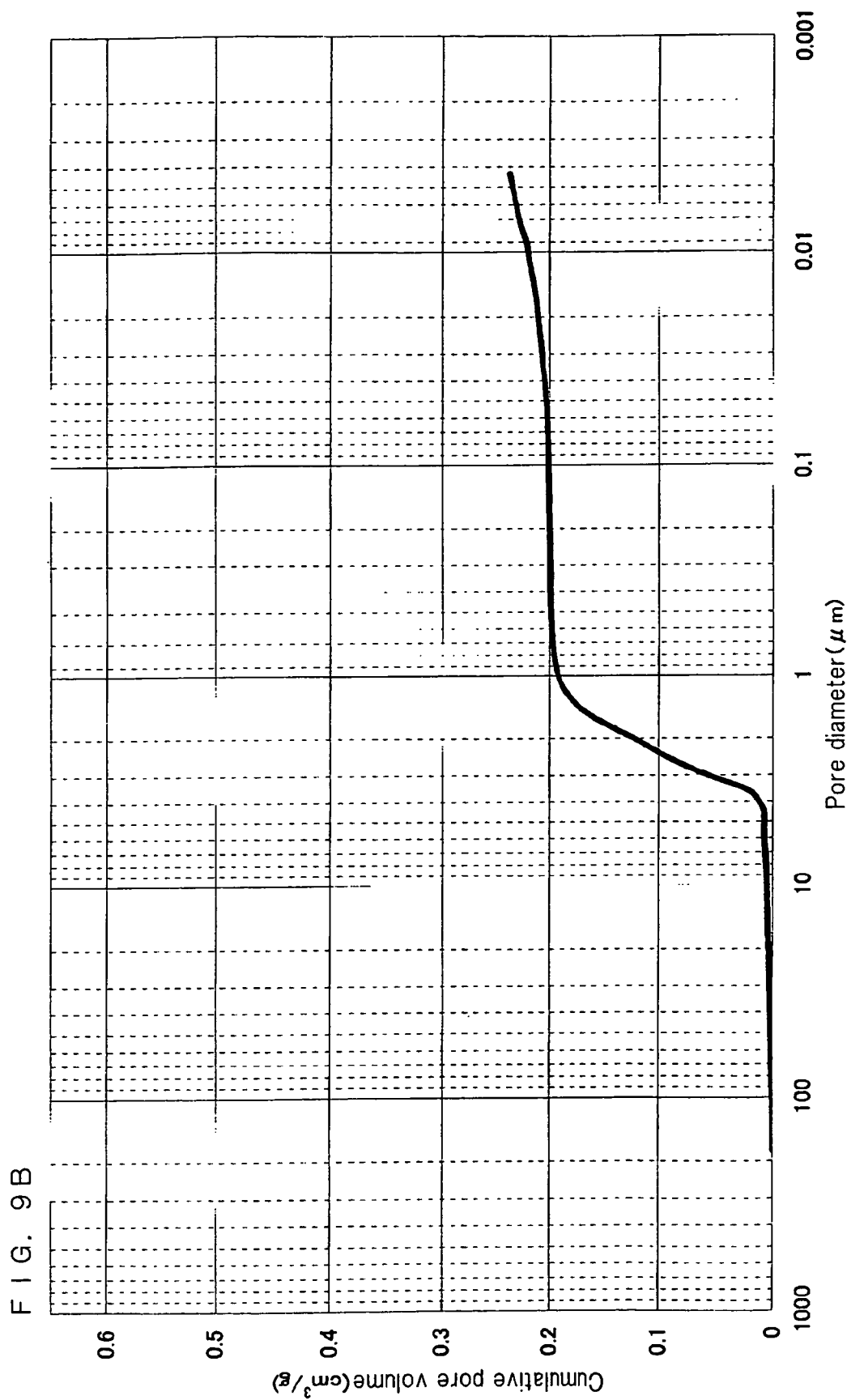
FIG. 9B is a graph showing the pore distribution (cumulative pore volume) of carrier I used in Control 5.

Catalyst I for the production of ethylene oxide was prepared in accordance with the similar procedure as in above Example 1, except that carrier I having the pore distribution shown in FIG. 9A and FIG. 9B was used and the amount of cesium nitrate to be added was altered to 1.5 g. Catalyst I was poor in performance and burned out before the conversion of ethylene reached 10% giving no result.

(Control 6)

Figure 10A:
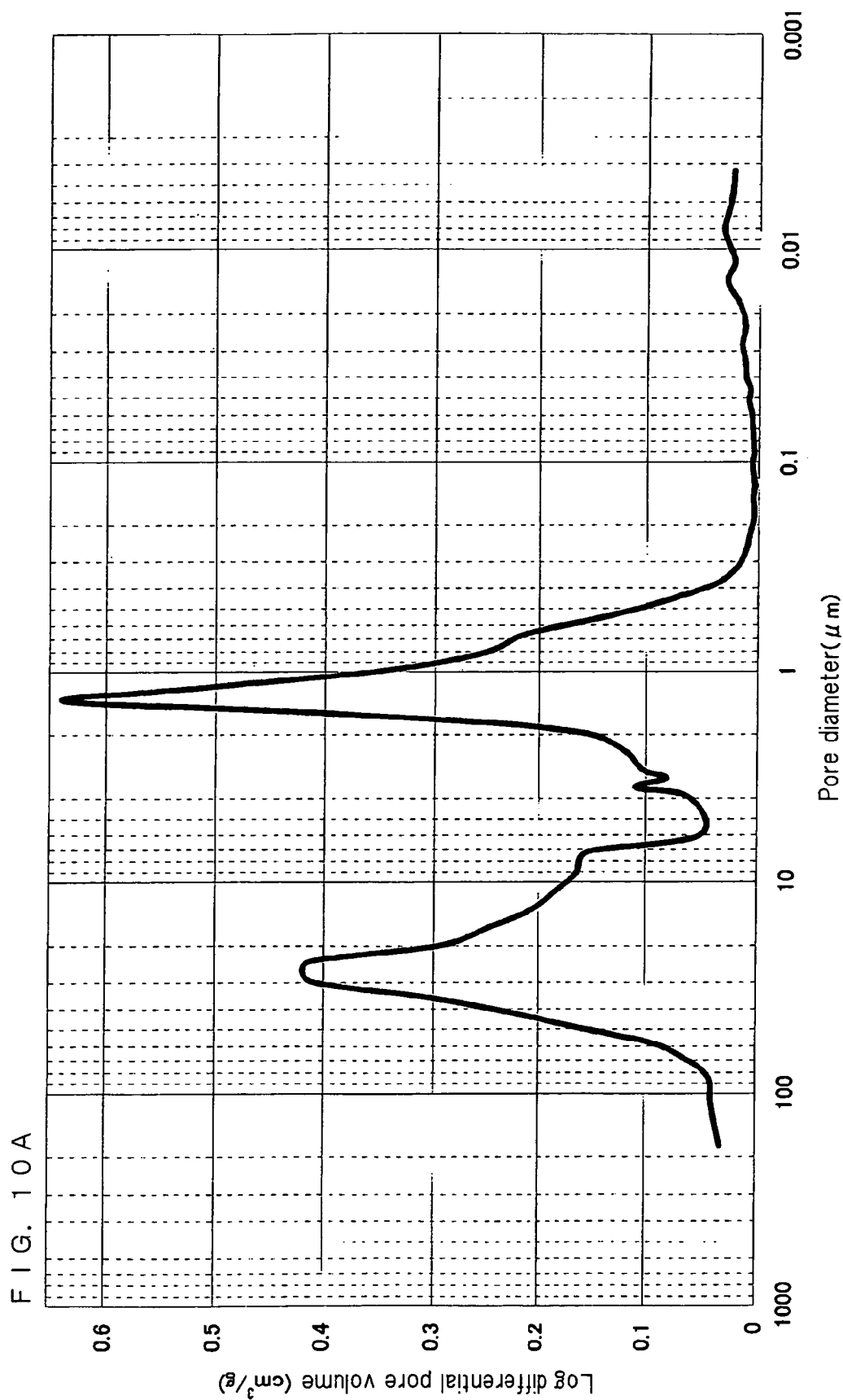
FIG. 10A is a graph showing the pore distribution (log differential pore volume) of carrier J used in Control 6.
Figure 10B:
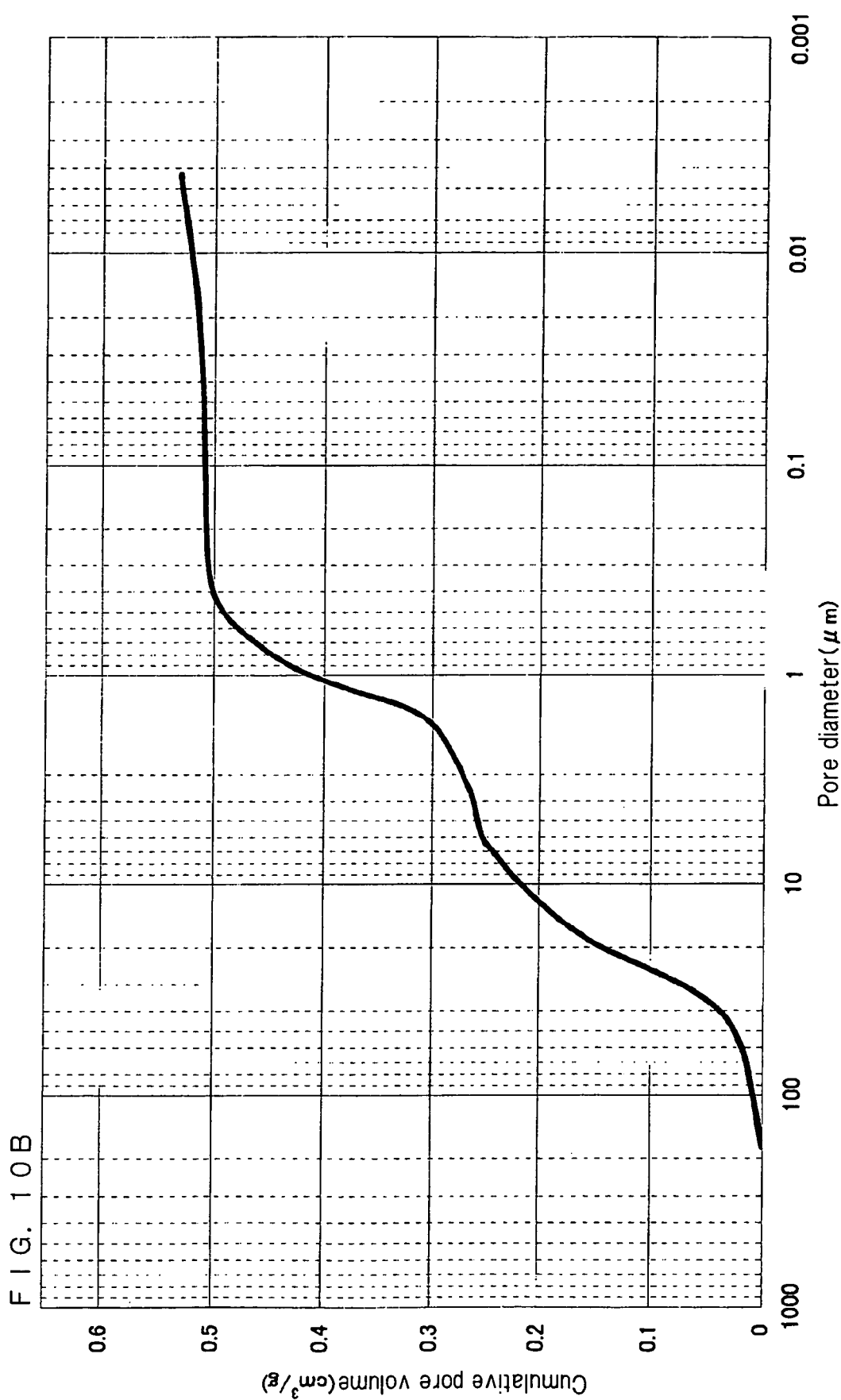
FIG. 10B is a graph showing the pore distribution (cumulative pore volume) of carrier J used in Control 6.

Catalyst J for the production of ethylene oxide was prepared in accordance with the similar procedure as in above Example 1, except that carrier J having the pore distribution shown in FIG. 10A and FIG. 10B was used and the amount of cesium nitrate to be added was altered to 1.5 g.

As apparent from the results shown in above Table 1, this invention can provide a catalyst for the production of ethylene oxide having excellent selectivity. The method for the production of ethylene oxide using the above catalyst enables ethylene oxide to be produced in a high yield.

This application is based on JP-Application Number-2006-268957 filed on Sep. 29, 2006, the entire contents, wherein are hereby incorporated by reference.

What is claimed is:

1. A catalyst for the production of ethylene oxide, comprising: a carrier containing α-alumina as the main component which has at least two log differential pore volume distribution peaks in a pore diameter range of 0.01-100 μm and at least one peak of the above peaks is present in a pore diameter range of 0.01-1.0 μm in the pore distribution measured by mercury porosimetry, wherein each peak is a maximum value of the log differential pore volume distribution of 0.2 cm$^3$/g or larger, and a catalyst component comprising silver is supported on the carrier.

2. The catalyst for the production of ethylene oxide according to claim 1, wherein the specific surface area of said carrier is 0.03-10 m²/g.

3. The catalyst for the production of ethylene oxide according to claim 1, wherein the pore volume of said carrier is 0.2-0.6 cm³/g.

4. The catalyst for the production of ethylene oxide according to claim 1, wherein the ratio of the pore volume of the pore having a pore diameter of 0.1-0.5 µm relative to the total pore volume of said carrier is 5-50 vol %.

5. The catalyst for the production of ethylene oxide according to claim 1, wherein the median pore diameter of said carrier is 0.1-10 µm.

6. The catalyst for the production of ethylene oxide according to claim 1, wherein the water absorption of said carrier is 10-70%.

7. The catalyst for the production of ethylene oxide according to claim 1, wherein the primary particle diameter of the α-alumina, the raw material of said carrier is 0.01-100 µm, and the secondary particle diameter is 0.1-1,000 µm.

8. The catalyst for the production of ethylene oxide according to claim 1, wherein the mean diameter of said carrier is 3-20 mm.

9. The catalyst for the production of ethylene oxide according to claim 1, wherein the content of the α-alumina in said carrier is 90 mass % or more relative to the total mass of the carrier.

10. The catalyst for the production of ethylene oxide according to claim 1, wherein the content of an oxide of an alkali metal or an alkaline-earth metal in said carrier is 0-5 mass % in terms of the oxide relative to the total mass of the carrier.

11. The catalyst for the production of ethylene oxide according to claim 1, wherein the content of an oxide of a transition metal in said carrier is 0-5 mass % in terms of the oxide relative to the total mass of the carrier.

12. The catalyst for the production of ethylene oxide according to claim 1, wherein the content of silica in said carrier is 0.01-10.0 mass % relative to the total mass of the carrier.

13. The catalyst for the production of ethylene oxide according to claim 1, wherein said catalyst component includes cesium as a reaction promoter.

14. The catalyst for the production of ethylene oxide according to claim 1, wherein an amount of silver to be supported as said catalyst component is 1-30 mass % relative to the mass of the catalyst for the production of ethylene oxide.

15. The catalyst for the production of ethylene oxide according to claim 1, wherein an amount of said reaction promoter to be supported is 0.001-2 mass % relative to the mass of the catalyst for the production of ethylene oxide.

16. A method for the production of ethylene oxide comprising conducting catalytic vapor phase oxidation of ethylene with a molecular oxygen-containing gas in a gas phase with a gas containing molecular oxygen in the presence of the catalyst according to claim 1.

* * * * *